(12) United States Patent
Woodruff et al.

(10) Patent No.: US 8,772,029 B2
(45) Date of Patent: Jul. 8, 2014

(54) MODULATION OF OOCYTE MEIOTIC PROGRESSION AND OOCYTE ACTIVATION

(75) Inventors: Teresa K. Woodruff, Chicago, IL (US); Thomas V. O'Halloran, Chicago, IL (US); Miranda L. Bernhardt, Chicago, IL (US); Betty Y. Kong, Chicago, IL (US); Alison M. Kim, Bethesda, MD (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/548,326

(22) Filed: Jul. 13, 2012

(65) Prior Publication Data

US 2013/0017602 A1 Jan. 17, 2013

Related U.S. Application Data

(60) Provisional application No. 61/508,135, filed on Jul. 15, 2011.

(51) Int. Cl.
*C12N 5/00* (2006.01)
*C12N 5/02* (2006.01)

(52) U.S. Cl.
USPC .......................................... 435/375; 435/325

(58) Field of Classification Search
USPC ................................................. 435/375, 325
See application file for complete search history.

(56) References Cited

PUBLICATIONS

Sakurai et al. Temporary Developmental Arrrest After Storage of Fertilized Mouse Oocytes At 4 Degrees Celsius: Effects on Embryonic Development, Maternal mRNA Processing and Cell Cycle; Molecular Human Reproduction, vol. 11, No. 5 (2005) pp. 325-333.*
De Vos, A. Intracytoplasmic Sperm Injection (ICSI); Human Reproduction, vol. 15 (Suppl. 4) (2000) pp. 59-64.*
Bernhardt et al., "Zinc requirement during meiosis I-meiosis II transition in mouse oocytes is independent of the MOS-MAPK pathway," Biol. Reprod, 2011, 84: 526-536.
Berhnhardt et al., "A zinc-dependent mechanism regulates meiotic progression in mammalian oocytes," Biol Reprod, 2012, 86(4):114.
Ducibella et al., "The roles of Ca2+, downstream protein kinases, and oscillatory signaling in regulating fertilization and the activation of development," Dev Biol, 2008, 315: 257-279.
Dumont et al., "p90Rsk is not involved in cytostatic factor arrest in mouse oocytes," J Cell Biol, 2005, 169: 227-231.
Eppig et al., "Genetic regulation of traits essential for spontaneous ovarian teratocarcinogenesis in strain LT/Sv mice: aberrant meiotic cell cycle, oocyte activation, and parthenogenetic development," Cancer Res, 1996, 56: 5047-5054.
Gautier et al., "Cyclin is a component of maturation-promoting factor from Xenopus," Cell, 1990, 60: 487-494.
Hansen et al., "CaMKII and polo-like kinase 1 sequentially phosphorylate the cytostatic factor Emi2/XErp1 to trigger its destruction and meiotic exit," Proc Natl Acad Sci USA, 2006, 103: 608-613.
Hashimoto et al., "Parthenogenetic activation of oocytes in c-mos-deficient mice," Nature, 1994, 370: 68-71.
Holt et al., "Spatial regulation of APCCdh1-induced cyclin B1 degradation maintains G2 arrest in mouse oocytes," Development, 2010, 137: 1297-1304.
Ibanez et al., "Genetic strain variations in the metaphase-II phenotype of mouse oocytes matured in vivo or in vitro," Reproduction, 2005, 130: 845-855.
Igarashi et al., "Alterations of PLCbeta1 in mouse eggs change calcium oscillatory behavior following fertilization," Dev Biol, 2007, 312: 321-330.
Inoue et al., "A direct link of the Mos-MAPK pathway to Erp1/Emi2 in meiotic arrest of *Xenopus laevis* eggs," Nature, 2007, 446: 1100-1104.
Kim et al., "Zinc sparks are triggered by fertilization and facilitate cell cycle resumption in mammalian eggs," ACS Chem Biol, 2011, 6(7):716-723.
Kim et al., "Zinc availability regulates exit from meiosis in maturing mammalian oocytes," Nat Chem Biol, 2010, 6: 674-681.
Kubiak et al., "The metaphase II arrest in mouse oocytes is controlled through microtubule-dependent destruction of cyclin B in the presence of CSF," EMBO J, 1993, 12: 3773-3778.
Laemmli et al., "Cleavage of structural proteins during the assembly of the head of bacteriophage T4," Nature, 1970, 227(5259): 680-685.
Levran et al., "Maturation arrest of human oocytes as a cause of infertility: case report," Hum Reprod, 2002, 17: 1604-1609.
Liu et al., "Calcium elevation at fertilization coordinates phosphorylation of XErp1/Emi2 by Plx1 and CaMK II to release metaphase arrest by cytostatic factor," Curr Biol, 2005, 15: 1458-1468.
Liu et al., "The anaphase-promoting complex/cyclosome inhibitor Emi2 is essential for meiotic but not mitotic cell cycles," J Biol Chem, 2006, 281: 34736-34741.
Lohka et al., "Purification of maturation-promoting factor, an intracellular regulator of early mitotic events," Proc Natl Acad Sci USA, 1988, 85: 3009-3013.
Madgwick et al., "How eggs arrest at metaphase II: MPF stabilisation plus APC/C inhibition equals Cytostatic Factor," Cell Division, 2007, 2: 4.
Madgwick et al., "Maintenance of sister chromstid attachment in mouse eggs through maturation-promoting factor activity," Dev Biol, 2004, 275: 68-81.
Madgwick et al., "Mouse Emi2 is required to enter meiosis II by reestablishing cyclin B1 during interkinesis," J Cell Biol, 2006, 174: 791-801.
Matsui et al., "Cytoplasmic control of nuclear behavior during meiotic maturation of frog oocytes," J Exp Zool, 1971, 177:129-145.
Morgan et al., "Principles of CDK regulation," Nature, 1995, 374: 131-134.
Murray et al., "The role of cyclin synthesis and degradation in the control of maturation promoting factor activity," Nature, 1989, 339: 280-286.
Nishiyama et al., "Phosphorylation of Erp1 by p90rsk is required for cytostatic factor arrest in *Xenopus laevis* eggs," Nature, 2007, 446: 1096-1099.

(Continued)

*Primary Examiner* — Susan Hanley
*Assistant Examiner* — Paul Martin
(74) *Attorney, Agent, or Firm* — Casimir Jones S.C.

(57) ABSTRACT

The present invention provides methods, compositions, and systems for reinitiating meiosis in cells in meiotic arrest and oocyte activation in fertilized, but un-activated, oocytes. In certain embodiments, Zn-binding moieties (e.g., zinc chelators) are used for reinitiating meiosis or oocyte activation.

7 Claims, 17 Drawing Sheets

(56) References Cited

PUBLICATIONS

Ohe et al., "Erp1/Emi2 is essential for the meiosis I to meiosis II transition in *Xenopus* oocytes," Dev Biol, 2007, 303: 157-164.

Perry et al., "Second meiotic arrest and exit in frogs and mice," EMBO reports, 2008, 9: 246-251.

Rauh et al., "Calcium triggers exit from meiosis II by targeting the APC/C inhibitor XErp1 for degradation," Nature, 2005, 437: 1048-1052.

Schindler et al., "CDC14B acts through FZR1 (CDH1) to prevent meiotic maturation of mouse oocytes," Biol Reprod, 2009, 80: 795-803.

Schmidt et al., "*Xenopus* polo-like kinase Plx1 regulates XErp1, a novel inhibitor of APC/C activity," Genes Dev, 2005, 19: 502-513.

Schmidt et al., "Cytostatic factor: an activity that puts the cell cycle on hold," J Cell Sci, 2006, 119: 1213-1218.

Shoji et al., "Mammalian Emi2 mediates cytostatic arrest and transduces the signal for meiotic exit via Cdc20," EMBO J, 2006, 25: 834-845.

Suzuki et al., "Mouse Emi2 as a distinctive regulatory hub in second meiotic metaphase," Development, 2010a, 137: 3281-3291.

Suzuki et al., "Full-term mouse development by abolishing $Zn^{2+}$-dependent metaphase II arrest without $Ca^{2+}$ release," Development, 2010b, 137:2659-2669.

Svoboda et al., "Selective reduction of dormant maternal mRNAs in mouse oocytes by RNA interference," Development, 2000, 127: 4147-4156.

Tsurumi et al., "The spindle assembly checkpoint is not essential for CSF arrest of mouse oocytes," J Cell Biol, 2004, 167: 1037-1050.

Tung et al., "A role for the anaphase-promoting complex inhibitor Emi2/XErp1, a homolog of early mitotic inhibitor 1, in cytostatic factor arrest of *Xenopus* eggs," Proc Natl Acad Sci USA, 2005, 102: 4318-4323.

Wu et al., "Across the meiotic divide—CSF activity in the post-Emi2/XErp1 era," J Cell Sci, 2008, 121: 3509-3514.

Xu, et al., "Tissue-engineered follicles produce live, fertile offspring.," Tissue Eng, 2006,12(10):2739-46.

* cited by examiner

MODULATION OF OOCYTE MEIOTIC PROGRESSION AND OOCYTE ACTIVATION

The present application claims priority to U.S. Provisional Application Ser. No. 61/508,135 filed Jul. 15, 2011, which is herein incorporated by reference in its entirety.

This invention was made with government support under P01 HD021921 awarded by the National Institutes of Health. The government has certain rights in the invention.

FIELD OF THE INVENTION

The present invention relates to methods, compositions, and systems for reinitiating meiosis in cells in meiotic arrest and oocyte activation in fertilized, but un-activated, oocytes. In certain embodiments, Zn-binding moieties (e.g., zinc chelators) are used for reinitiating meiosis or oocyte activation.

BACKGROUND

In assisted reproductive technology (ART), only mature eggs that reach metaphase-II stage (MII) are capable of becoming fertilized and developing as embryos, while not-fully-mature oocytes that do not attain this stage must typically be discarded. In some patients, most or all oocytes recovered for ART treatments display a maturation arrest, leading to very poor fertilization rates (Levran et al 2002). What is needed, therefore, are methods and compositions that allow immature oocytes, arrested in pre-MII stage, to be reactivated and proceed to the MII stage.

SUMMARY OF THE INVENTION

The present invention provides methods, compositions, and systems for reinitiating meiosis in cells in meiotic arrest and oocyte activation in fertilized, but un-activated, oocytes. In certain embodiments, Zn-binding moieties (e.g., zinc chelators) are used for reinitiating meiosis or oocyte activation.

In some embodiments, the present invention provides methods for resuming meiosis in an arrested cell comprising: treating a cell (e.g., oocyte) in meiotic arrest with a Zn-binding moiety such that meiosis is resumed. In particular embodiments, the methods further comprise contacting the cell with zinc replete medium (or supplementing the media the cell is in) such that the cell progresses from a first phase to a second phase. In further embodiments, the first phase is metaphase I (MI) and the second phase is metaphase II (MII). In particular embodiments, the first phase is germinal vesicle (GV) phase and the second phase is metaphase II (MII) or any other phase after GV. In particular embodiments, the Zn-binding moiety is configured to coordinate one or more Zn ions.

In some embodiments, the present invention provides methods of oocyte activation comprising: treating a fertilized, but un-activated, oocyte with a Zn-binding moiety such that oocyte activation occurs (e.g., such that an embryo forms, such as a 2-cell embryo). In certain embodiments, the oocyte is initially un-activated due to lack of sperm PLC activity. In other embodiments, the oocyte is fertilized by in-vitro fertilization (IVF) methods. In some embodiments, the oocyte is fertilized by cytoplasmic sperm injection (ICSI). In additional embodiments, the Zn-binding moiety is configured to coordinate one or more Zn ions.

In particular embodiments, the present invention provides systems and compositions comprising: a) a cell (e.g., oocyte) in meiotic arrest or a fertilized, but unactivated, oocyte; and b) a Zn-binding moiety. In some embodiments, the systems and compositions further comprise: c) a zinc-replete medium. In particular embodiments, the cell in meiotic arrest. In other embodiments, the cell is in metaphase I (MI). In further embodiments, the cell is in the germinal vesicle stage. In particular embodiments, the oocyte is an in-vitro fertilized oocyte. In other embodiments, the oocyte is a cytoplasmic sperm injected oocyte.

DESCRIPTION OF THE FIGURES

FIG. 1B is a western blot analysis for CCNB1 and EMI2. FIG. 1C shows histone H1 kinase activity of oocytes from the same treatment. Western blots were repeated at least 3 times, showing similar results. Graph presents densitometric analysis for at least 7 individual oocytes per group. Error bars show SEM and letters indicate significant differences according to ANOVA with Bonferroni post-hoc test (P<0.001).

FIG. 2B is a graph of histone H1 kinase activity showing densitometric analysis for at least 6 individual oocytes per group. Error bars show SEM and letters indicate significant differences according to ANOVA with Bonferroni post-hoc test (P<0.01).

DETAILED DESCRIPTION

Figure 1A:
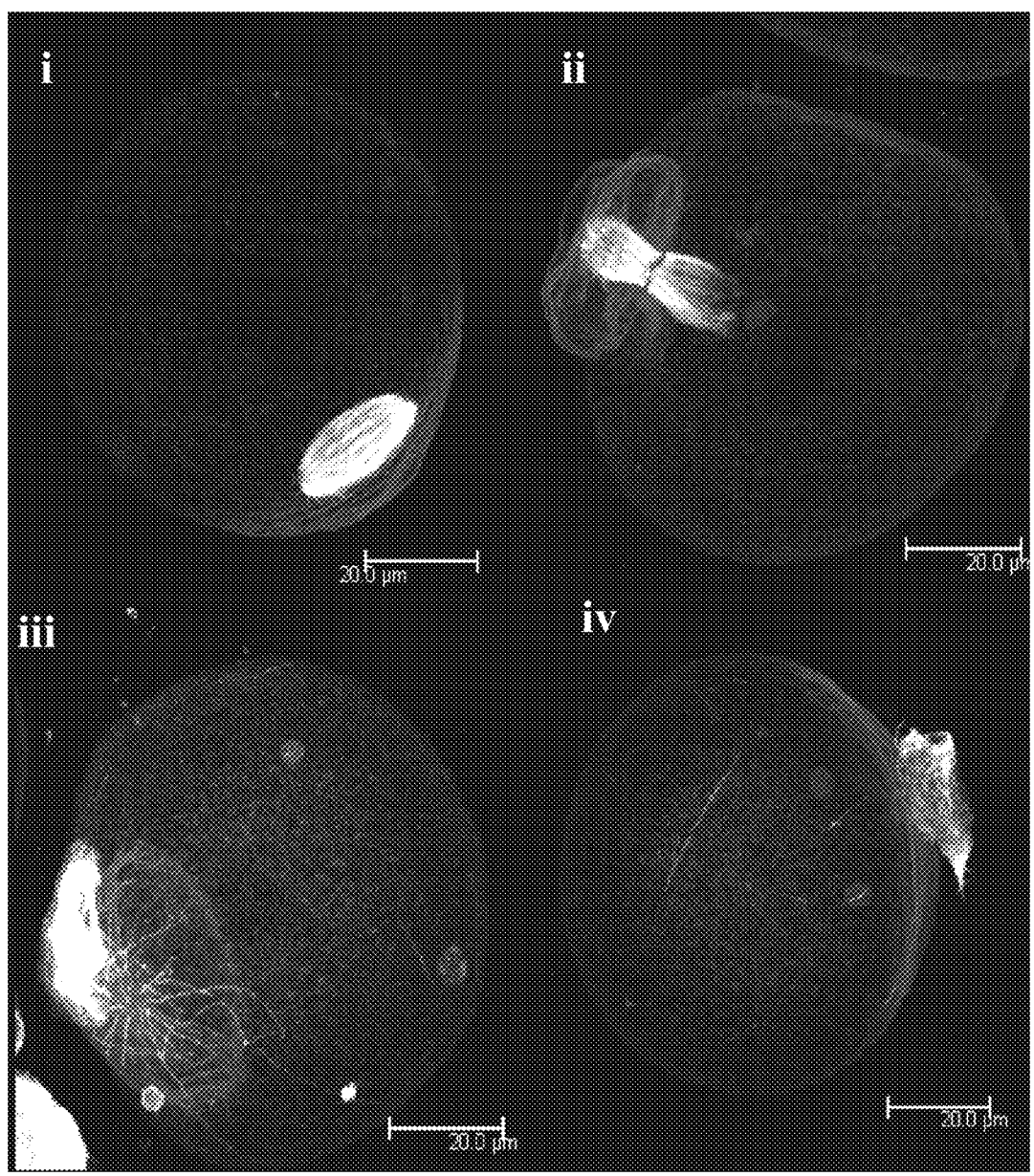
FIGS. 1A-C show zinc is required for successful MI-MII transition. COCs were cultured in control medium for 7.5 h and transferred to TPEN containing medium at MI for an additional 6.5 h followed by removal of cumulus cells. Spindle stains show that rather than forming normal MII spindles of controls (FIG. 1A, i), 31% of treated oocytes were arrested at telophase-I (FIG. 1A, ii), while 54% had a single chromatin mass without complete retention of midbody microtubules (FIG. 1A, iii). Others had multiple chromatin masses (FIG. 1A, iv) or failed to complete cytokinesis. Three-dimensional projections of confocal Z stacks with actin, tubulin, and DAPI shown in contrast. Bar=20 μm.

The present invention provides methods, compositions, and systems for reinitiating meiosis in cells in meiotic arrest and oocyte activation in fertilized, but un-activated, oocytes.

In certain embodiments, Zn-binding moieties (e.g., zinc chelators) are used for reinitiating meiosis or oocyte activation. In certain embodiments, the present invention provides for the manipulation of zinc availability (e.g., through chelation), as a tool to control the progression of oocyte meiosis. Such a tool is useful in the field of assisted reproductive technology (ART) to improve outcomes of oocyte in vitro maturation (IVM) and in vitro fertilization (IVF)/intracytoplasmic sperm injection (ICSI) in cases of meiotic arrest or uncoordinated nuclear and cytoplasmic maturation.

In assisted reproductive technology (ART), only mature eggs that reach metaphase-II stage (MII) are capable of becoming fertilized and developing as embryos, while not-fully-mature oocytes that do not attain this stage must typically be discarded. In some patients, most or all oocytes recovered for ART treatments display a maturation arrest, leading to very poor fertilization rates (Levran et al 2002). It has recently been shown that during the course of maturation from a germinal vesicle (GV)-intact oocyte to a mature MII egg, intracellular zinc content increases by over 50%, and that much of this accrued zinc is subsequently lost after fertilization and development to the 2-cell embryo stage (Kim et al 2010). These dynamics in zinc appear to be critical to progression of the oocyte through the meiotic maturation process, as treatment with the heavy metal chelator N,N,N',N'-tetrakis(2-pyridylmethyl)ethylenediamine (TPEN) during the MI-MII transition causes meiotic arrest at telophase-I (Kim et al 2010, Bernhardt et al 2011, Bernhardt et al manuscript in preparation). In addition, decreasing zinc availability in the MII-arrested egg using TPEN causes egg activation and resumption of cell cycle, and the use of zinc ionophores to increase intracellular zinc prevents this cell cycle resumption from occurring when eggs are treated with activating agents that increase intracellular calcium (Kim et al 2011, Suzuki et al 2010). Worked conducted during development of embodiments of this invention found that zinc may be involved in the control of earlier stages of meiotic re-initiation and exit from prophase-I arrest; TPEN treatment of oocytes held at GV stage using phosphodiesterase inhibitors causes a phenotype of premature GV breakdown (GVBD) and meiotic progression.

The present invention, including the Example below, show that zinc plays a critical and previously unrecognized role in the control of meiotic progression in the mammalian oocyte. As such, in certain embodiments, zinc-based binding moieties are used to modulate meiotic progression to overcome meiotic arrests at several stages observed clinically. In certain embodiments, zinc binding moieties are used for the production of fertilizable gametes in cases where oocytes collected are arrested and would currently be considered unusable with existing technologies.

In certain embodiments, the present invention provides for the use of treatments that modulate zinc availability in order to control the progression of oocyte meiosis. These methods are of value to the field of assisted reproductive technology by providing a means to overcome meiotic arrests that can otherwise prevent oocytes from reaching a fertilizable point in their maturation. In some embodiments, the present invention involves the use of zinc chelation (e.g., through intracellular, extracellular, or substrate-attached chelators) to limit zinc availability and promote progression through specific meiotic arrest points.

In certain embodiments, the methods of the present invention are for: i) use during in vitro maturation to overcome meiotic arrest at metaphase I (MI); ii) use during in vitro maturation to overcome meiotic arrest at the germinal vesicle (GV) stage; iii) use during in vitro maturation to coordinate nuclear and cytoplasmic maturation; and iv) use in combination with intracellular cytoplasmic sperm injection (ICSI) or in vitro fertilization (IVF) to achieve egg activation in the case of failure to activate due to lack of sperm PLC activity.

In certain embodiments, zinc modulation is useful for overcoming earlier meiotic arrests. Normally, treatment of GV stage oocytes with broad-spectrum or PDE3-specific phosphodiesterase (PDE) inhibitors results in maintenance of GV arrest due to elevated cAMP levels. Work conducted during the development of embodiments of the present invention has shown that TPEN treatment of these PDE-inhibitor arrested GV oocytes causes premature meiotic progression and GV breakdown (GVBD). When oocytes that have resumed meiosis are transferred back to zinc replete medium, a proportion of these oocytes progress to MII. As such, limiting zinc availability could also be used to overcome GV arrest and allow progression through GVBD in clinical cases of GV arrest. The methods of the present invention are also useful as a secondary treatment for oocytes that remain GV arrested following conventional in vitro maturation, and could be of particular value for use in conjunction with in vitro follicle culture systems currently being developed for use in fertility preservation programs for patients undergoing fertility-threatening cancer treatments, in which methods for overcoming GV arrest are necessary (Xu et al 2006).

In certain embodiments, modulation of zinc could be used to control meiotic progression in order to better coordinate events of nuclear maturation (progression through meiosis) with events of cytoplasmic maturation (those involved in preparing the egg for fertilization and successful development as an embryo) (reviewed in Eppig 1996). As our understanding of specific features of cytoplasmic maturation progresses, these techniques could provide ways to adjust the timing of nuclear maturation to align with the state of cytoplasmic maturation to produce optimally competent eggs.

In certain embodiments, TPEN treatment and/or other means of limiting zinc availability in the MII egg could be used to achieve egg activation in cases of failed activation following fertilization or ICSI (potentially due to deficient sperm PLC activity). This method for activation of embryonic development could also be of value to the field of somatic cell nuclear transfer for use in research and agricultural applications. Overall, modulation of zinc availability as a means of controlling progression through oocyte meiosis has many potentially beneficial applications.

The methods and compositions of the present invention provide fertility clinics and other centers providing assisted reproductive services with methods to treat oocytes and eggs displaying maturation arrests, promoting meiotic progression to ultimately produce fertilizable eggs capable of undergoing embryonic development. Other applications in reproductive technology include for use in livestock production and veterinary applications.

The present invention is not limited by the Zn-binding moiety employed. In some embodiments, a Zn-binding moiety is a chemical moiety capable of stably interacting with one or more Zn ions. In some embodiments, a Zn-binding group is capable of interacting with one or more Zn ions, while covalently attached to the other functional elements. In some embodiments, a Zn-binding moiety interacts with a Zn ion through covalent and/or non-covalent binding. In some embodiments, a Zn-binding moiety coordinates and/or partially coordinates a Zn ion. In some embodiments, a Zn-binding moiety is capable of coordinating a single Zn ion. In some embodiments, a Zn-binding moiety is capable of coordinating more than one Zn ions at a time (e.g., 2, 3, 4, 5, 6, 7, 8, 9, 10 . . . 20 . . . 50 . . . 100 . . . 1000, etc.). In some embodiments, a Zn-binding moiety comprises a functional group capable of transiently or stably binding, coordinating, and/or chelating one or more Zn ions (e.g., free or in another complex). In some embodiments, a Zn-binding moiety is Zn specific. In some embodiments, a Zn-binding moiety preferentially binds Zn over other metal ions. In some embodiments, a Zn-binding moiety is a general metal-binding moiety. Chemical moieties that find use as Zn-binding moieties include, but are not limited to, TPEN, diethyldithiocarbamate (DEDTC) and ethylenediaminetetra-acetic acid (EDTA), 1,10-phenanthroline, pyridyl-containing compounds, amine-containing compounds (e.g., tertiary amines), histidine containing compounds, sulfonamide-containing compounds, etc. In some embodiments, the Zn-binding moiety is TPEN. In some embodiments, a Zn-binding group has at least one functional group selected from polyalkylene oxide, hydroxylated group, or a group having at least one amine, ammonium salt, carboxylate, sulfanyl, sulfinyl, sulfonyl, phosphate, phosphonate, phosphate, tertiary amine, pyridyl group; or combinations thereof. In some embodiments, Zn-binding moiety comprises one or more sites for attachment to other functional groups.

EXAMPLES

Example 1

Modulation of Oocyte Meiotic Progression

This Example describes experiments conducted to determine the components involved in oocyte meiotic progression, including progression based on zinc availability.

Materials and Methods

Reagents and Antibodies

Anti-cyclinB1 antibody (ab72) was purchased from Abcam (Cambridge, MA). The anti-FBXO43 (Emi2) antibody (EB06061) was from Everest Biotech (Oxfordshire, UK). Culture medium, fetal bovine serum (FBS), rhodamine-phalloidin (R415), AlexaFluor-488 conjugated goat anti-mouse IgG (A11001), and horseradish peroxidase (HRP) conjugated anti-mouse IgG (62-6520) were purchased from Invitrogen (Carlsbad, CA). Peroxide conjugated anti-goat IgG (PI-9500) and VECTASHIELD mounting medium with 4',6-diamidino-2-phenylindole (DAPI) were from Vector Laboratories (Burlingame, CA). HRP conjugated anti-rabbit IgG (NA934) and ECL-Advanced detection reagent were purchased from Amersham Biosciences (Piscataway, NJ). Anti-a-tubulin (T9026 for immunofluorescence, T6199 for western blot) and all other chemicals and reagents not specifically noted were purchased from Sigma-Aldrich (St. Louis, MO).

Animals

Mice of the CD1 strain were maintained in accordance with the policies of Northwestern University's Animal Care and Use Committee and the National Institutes of Health Guide for the Care and Use of Laboratory Animals. Mice were bred and housed within a controlled barrier facility within Northwestern University's Center for Comparative Medicine (Chicago, Ill.). They were provided with Teklad Global (Madison, Wis.) irradiated 2919 chow and water ad libitum. Mice were maintained on food free of soybean or alfalfa meal, therefore minimizing the impact of phytoestrogens. Humidity, temperature, and photoperiod (14L:10D) were kept constant.

Oocyte and Egg Collection and In Vitro Maturation (IVM)

For IVM studies, immature female CD1 mice (17 to 21 day old) were injected with 5IU equine chorionic gonadotropin (eCG) (Calbiochem, La Jolla, CA) in 100 µL sterile phosphate-buffered saline (PBS), intraperitoneally. After 44 to 48 hours, mice were anesthetized using isoflurane and euthanized by cervical dislocation. Dissected ovaries were placed in Leibovitz L-15 medium containing 1% FBS (L-15/FBS) and 0.2mM 3-isobutyl-1-methylxanthine (IBMX), and large antral follicles were punctured using 28 gauge needles to release cumulus oocyte complexes (COCs). COCs were washed through several drops of culture medium consisting of Minimum Essential Medium (MEM)-alpha with GLUTAMAX supplemented with 10% FBS, 1.5IU/mL human chorionic gonadotropin (hCG), and 5ng/mL epidermal growth factor and placed in culture medium with or without 10 µM N,N,N',N'-tetrakis(2-pyridylmethyl) ethylenediamine (TPEN). In some experiments Z-Leu-Leu-Leu-al (MG132) was added to culture medium at 20 µM. COCs were cultured in drops of pre-equilibrated medium covered with embryo quality mineral oil at 37° C. in 5% CO2 with a humid environment. Ovulated MII eggs were collected from 4 to 6 week old mice primed with 5IU PMSG followed 48 h later by 5IU hCG. Oviducts were dissected into L-15/FBS, and eggs were removed and treated with 0.03% (w/v) hyaluronidase to remove cumulus cells. Eggs were washed and cultured in potassium simplex optimized medium (KSOM) (Millipore, Billerica, MA) covered with embryo quality mineral oil at 37° C. in 5% $CO_2$.

SDS-PAGE and Western Blotting

Western blotting was performed essentially as previously described (Bernhardt et al., 2010). Briefly, 15 to 50 cumulus-denuded oocytes were transferred in a minimal amount of medium to microcentrifuge tubes and immediately lysed in 8 µL of 1x SDSPAGE Sample Buffer (Laemmli, 1970). SDS-PAGE gels were run using the Invitrogen NuPAGE system and transferred to Immobilon-P PVDF membranes (Millipore, Billerica, MA). Blocking and antibody incubations were in 2% w/v ECL Advanced Blocking Reagent (Amersham) in TBS-T (20mM Tris, pH7.4, 137mM NaC1, 0.1% Tween20 v/v). Anti-CCNB1antibody was diluted 1:500, anti-FBXO43 was used at 1:1000 dilution, and anti-tubulin antibody was used at 1:10,000. HRP-conjugated secondary antibodies were diluted 1:10,000. Detection was performed using Amersham ECL Advanced detection reagent. BIOMAX MR films (Kodak, Rochester, NY) were exposed and developed, or an Alpha-Innotech (San Learndo, CA) MultiImage II system was used.

Immunofluorescence and Scanning Laser Confocal Microscopy

Oocytes were denuded of cumulus cells and fixed in a microtubule stabilizing buffer (Ibanez et al., 2005) containing 2% formaldehyde and 1% Triton X-100 for 30 min at 37° C. Oocytes were washed and blocked in PBS containing 0.1M glycine, 3mg/mL BSA, 0.01% Tween 20, and 0.01% sodium azide for at least 1 h and were stored in blocking solution at 4° C. for up to 2 weeks. Oocytes were incubated with anti-tubulin antibody (1:100) for 1 h at 37C. followed by three washes in blocking solution. They were then incubated for 1 h in AlexaFluor-488 conjugated anti-mouse secondary antibody (5µg/mL) and rhodamine-phalloidin (2U/mL), washed three additional times, and mounted in VECTASHIELD with DAPI. Microscopy was performed using a Leica SP5 inverted laser-scanning confocal microscope with a 63x oil immersion objective (Leica Microsystems, Heidelberg, Germany). Images were processed using LAS AF software (Leica Microsystems).

Histone H1 and MBP Kinase Assay Zone Name: a6,AMD

Histone H1 and myelin basic protein (MBP) dual kinase assays were performed as previously described (Svoboda et al., 2000). Dried gels were exposed to Kodak BIOMAX MR films for 12 to 72 hours at −80° C. using Kodak intensifying screens; films were developed, scanned, and analyzed using ImageJ software. Assays were performed on single oocytes, and densitometric analysis is expressed relative to levels in control eggs.

Plasmid Construction, In Vitro Transcription, Morpholinos, and siRNA

Empty pIVT vector was kindly provided by Richard Schultz (Igarashi et al., 2007). A full-length cDNA clone for Emi2 was obtained from the IMAGE collection (Thermo-Fischer, Open Biosystems, Hutsville, Ala.), and a missense mutation at codon 393 was corrected using Quickchange site-directed mutagenesis (Agilent). Full-length Emi2 sequence along with an N-terminal T7 tag were cloned into pIVT using XbaI and KpnI sites as a PCR-generated fragment. Emi2 sequence was also cloned into the MBP-fusion protein expression vector pMAL-c5x (New England Biolabs, Beverly, Mass.) using XmnI and BamHI sites. C573A mutations (TGC to GCC) of both vectors were produced using Agilent Quickchange, and confirmed by sequencing. The vector pRN3-CCNB1(Δ90)-EGFP was kindly provided by Karen Schindler (Schindler and Schultz, 2009). Plasmids were linearzed and capped RNA was produced using a mMESSAGE mMACHINE T3 Kit (Ambion, Austin, Tex.). RNA was purified with RNeasy columns (Qiagen, Valencia, Calif.) and eluted in 10 mM Tris, pH7.4, 0.1 mM EDTA at a final concentration of 0.5 µg/µL, and aliquots were stored at −80° C. Sequence of the Emi2 morpholino (MO) used has been previously published and validated (Madgwick et al., 2006). MOs purchased from Gene Tools (Philomath, Oreg.) were dissolved in molecular grade water at 5 mM, aliquotted and stored at −80° C., and heated to 65° C. for 10 min prior to injection. A pre-designed Emi2 siRNA was purchased from Ambion, dissolved in RNAse-free water at a concentration of 25 µM, aliquotted, and stored at −80° C.

Oocyte Microinjection

Microinjection was performed essentially as previously described (Bernhardt et al., 2010). GV intact oocytes were collected and manually denuded of cumulus cells in L-15/FBS containing 0.2 mM IBMX, then transferred to drops of L-15 medium containing 0.05% (w/v) polyvinyl alcohol (PVA) and 0.5% (v/v) penicillin-streptomycin (Invitrogen) under light mineral oil on a heated stage for injection. Injection of oocytes at the MI-MII transition was performed in medium without IBMX and with stage temperature turned down to 27 to 30° C.; 10 µM TPEN was included in holding medium where appropriate. Three to 10 pL of in vitro synthesized RNA, MO, or siRNA was injected into the oocyte cytoplasm using an Eppendorf FemtoJet pressure microinjector with Femtotip injection capillaries. GV stage oocytes were held in alpha-MEM containing IBMX and 1% FBS for 2-6 hours (depending on the experiment) before being transferred to IVM medium; MI-MII transition oocytes were returned to culture medium without IBMX. Following culture, oocytes were fixed for spindle staining or collected for Western blotting and kinase assays as described above.

Zinc Pyrithione (ZnPT) Treatments

Ovulated MII eggs were collected as described above. Eggs were transferred to KSOM medium with or without 10 μM ZnPT (1:1000 dilution of a 10 mM stock in DMSO) for exactly 5 minutes. Eggs were then washed in KSOM and allowed to recover for 10-15 minutes prior to activation. For $SrCl_2$ activation, eggs were transferred to drops of calcium-free KSOM containing 10 mM $SrCl_2$ for 2 hours, followed by 4 additional hours of culture in calcium-containing KSOM without $SrCl_2$. TPEN activation was performed as previously described (Kim et al., 2011); eggs were cultured for 6 hours in KSOM containing 10 μM TPEN. Unactivated controls were cultured in KSOM for the same 6 hour time period to assess levels of spontaneous parthenogenesis.

Results

Zinc Insufficiency Restricted to the MI-MII Transition Disrupts Meiotic Maturation It was first sought to narrow the time frame of meiotic maturation during which zinc is required to allow normal meiotic progression. Previous work has shown that limiting intracellular zinc availability using the heavy metal chelator TPEN led to failed asymmetric division, reduction in MPF activity and CCNB1 protein levels, and a telophase I arrest-like spindle phenotype (Bernhardt et al., 2010; Kim et al., 2010). When cumulus oocyte complexes (COCs) were matured in vitro under control conditions until MI spindles formed (7.5 h) and then transferred to medium containing 10 μM TPEN (for an additional 6.5 h of culture), these oocytes failed to form MII spindles, while oocytes kept in control medium throughout the 14 h culture matured normally and arrested at MII (FIG. 1, A; Table 1).

Table 1 shows that Zinc is required for successful MI-MII transition. Oocytes treated with TPEN during the MI-MII transition fail to enter MII. Following IVM under the conditions listed in control (C) or TPEN-containing (T) medium, oocytes were stained and imaged, and their spindle phenotypes were scored.

Figure 1B:
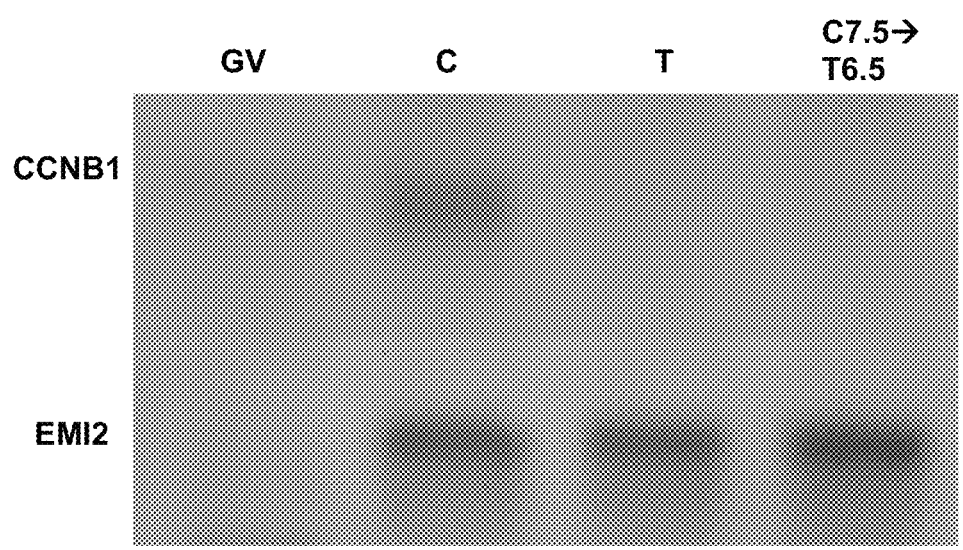
Figure 1C:
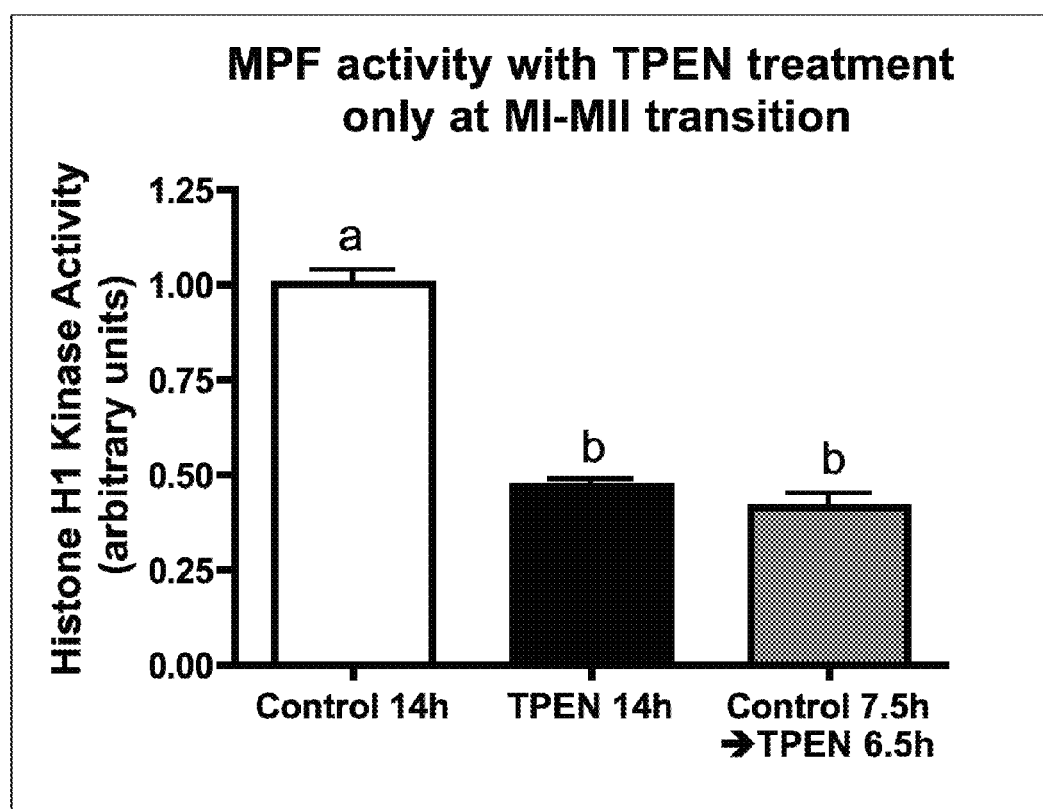

Of oocytes cultured in TPEN during the MI-MII transition, 31% had telophase I arrested spindles (FIG. 1, A.ii), and an additional 54% had chromatin masses rather than discrete chromosomes but without complete retention of a telophase microtubule conformation (FIG. 1, A.iii). Most of the remaining oocytes had >1 chromatin mass (FIG. 1, A.iv) or had not completed cytokinesis, and none had formed MII spindles. Western blot analysis and histone H1 kinase assays showed that CCNB1 protein levels and MPF activity are low in oocytes cultured with TPEN during the MI-MII transition (FIG. 1, B and C), as has been shown previously for oocytes matured for 12 to 16 h in the presence of TPEN (Bernhardt et al., 2010). Thus, zinc insufficiency limited to the MI-MII transition period causes a meiotic arrest phenotype and failure to reactivate MPF, leading us to conclude that intracellular zinc availability is required for normal MI-MII transition.

Proteasomal Inhibition Partially Rescues Zinc-Insufficient Oocytes

It has been previously shown that zinc-insufficient oocytes fail to increase MPF activity following the first meiotic division and have low CCNB1 protein levels (Bernhardt et al., 2010). In order to determine whether this decrease in CCNB1 is the major cause of the observed meiotic arrest phenotype, it was tested whether increasing CCNB1 would be sufficient to rescue MII entry in zinc-insufficient oocytes by inhibiting the proteasome at the end of the MI-MII transition, thereby halting CCNB1 degradation. Experimental oocytes were cultured for 10 hours in TPEN-containing medium and were then transferred into medium containing TPEN as well as the proteasome inhibitor Z-Leu-Leu-Leu-al (MG132) at 20 μM concentration. MG132 was added after first polar body extrusion, because earlier addition would result in MI arrest due to failure to degrade APC/C targets that prevent cell division. Oocytes were cultured for an additional 6 h in the presence of MG132 to allow time for CCNB1 reaccumulation, for a total 16 h IVM culture period. Proteasome inhibition led to a partial rescue of the zinc insufficiency phenotype. 69% of treated oocytes formed spindle-like structures, and none were in telophase I arrest, despite being cultured in the presence of TPEN for the entire culture period (FIG. 2, A; Table 2).

TABLE 1

|  | n | TPEN-like (telophase-I arrest-like) | partial TPEN-like (chromatin mass) | other (>2 chr. masses) | normal MII |
|---|---|---|---|---|---|
| Control 14 h | 29 | 0% | 0% | 0% | 100% |
| C 7.5 h → T 6.5 h | 42 | 31% | 54% | 19% | 0% |
| TPEN 14 h | 34 | 91% | 3% | 6% | 0% |

TABLE 2

|  | n | MII | spindle with ≤3 chr. out of place | spindle with chr. scattered along length | persisting midbody or chromatin mass | other | complete TPEN-like |
|---|---|---|---|---|---|---|---|
| Control 16 h | 16 | 100% | 0% | 0% | 0% | 0% | 0% |
| T 10 h → T + MG132 6 h | 26 | 19% | 31% | 19% | 15% | 15% | 0% |
| TPEN 16 h | 13 | 0% | 0% | 0% | 0% | 23% | 77% |

Table 2 shows proteasome inhibition partially rescues zinc insufficiency phenotype. A majority of zinc-insufficient oocytes treated with MG132 following the first meiotic division transition progress beyond telophase-I arrest and form MII spindle-like structures. Following IVM in control (C) or TPEN-containing (T) medium with or without addition of 20 µM MG132 after 10 h, oocytes were stained and imaged, and their spindle phenotypes were scored.

Figure 2A:
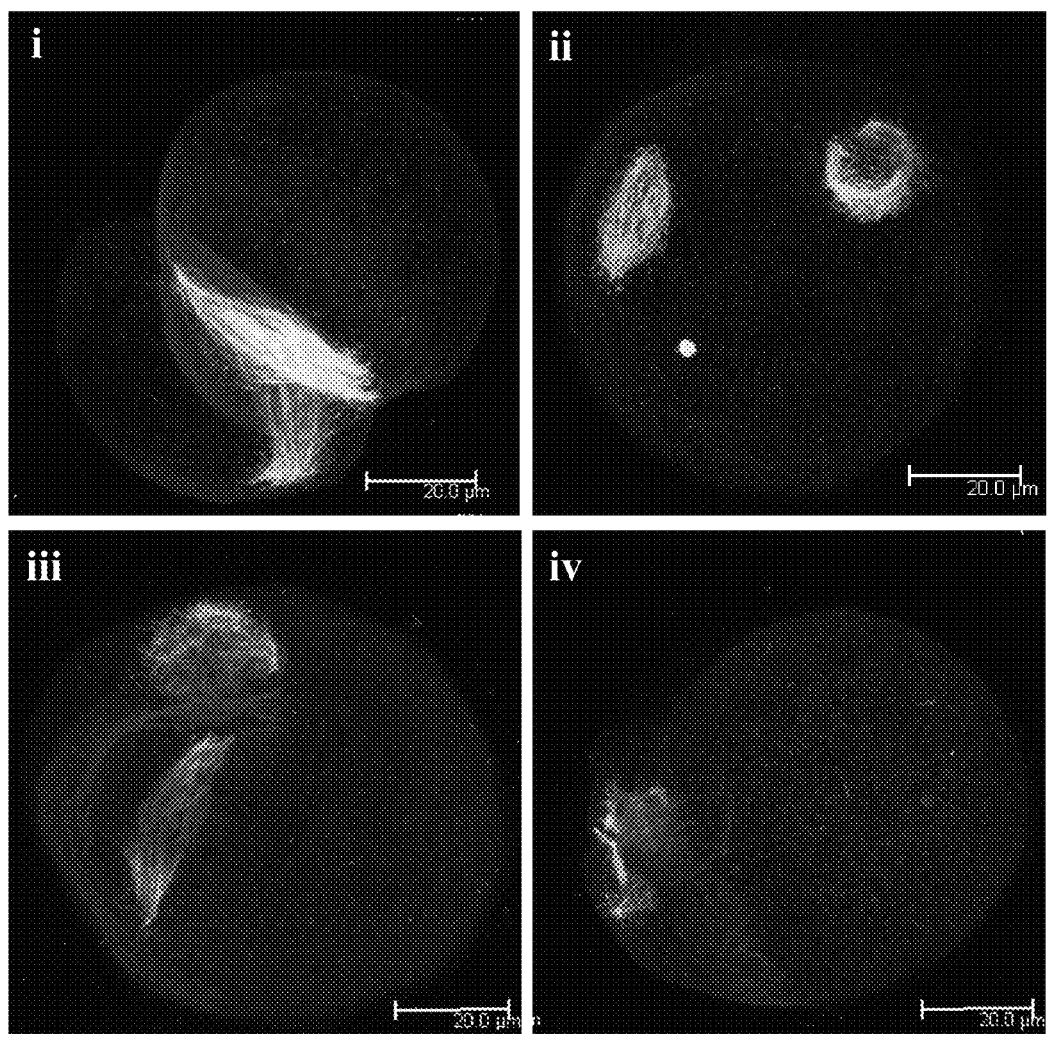
FIGS. 2A and 2B show proteasome inhibition partially rescues zinc insufficient phenotype. COCs were cultured in TPEN containing medium for 10 h and transferred to medium containing both TPEN and MG132 for an additional 6 h followed by removal of cumulus cells. Spindle stains show that 69% of oocytes had some degree of MII spindle formation, with 19% showing aligned metaphase plates (FIG. 2A, i), 31% with ≤3 misaligned chromosomes (FIG. 2A, ii), and 19% with >3 misaligned chromosomes (FIG. 2A, iii)). A majority of oocytes cultured in TPEN without MG132 for the entire culture period displayed the telophase-I arrested spindles associated with zinc insufficiency during IVM (FIG. 2A, iv). Three-dimensional projections of confocal Z stacks with actin, tubulin, and DAPI shown in contrast. Bar=20 μm.
Figure 2B:
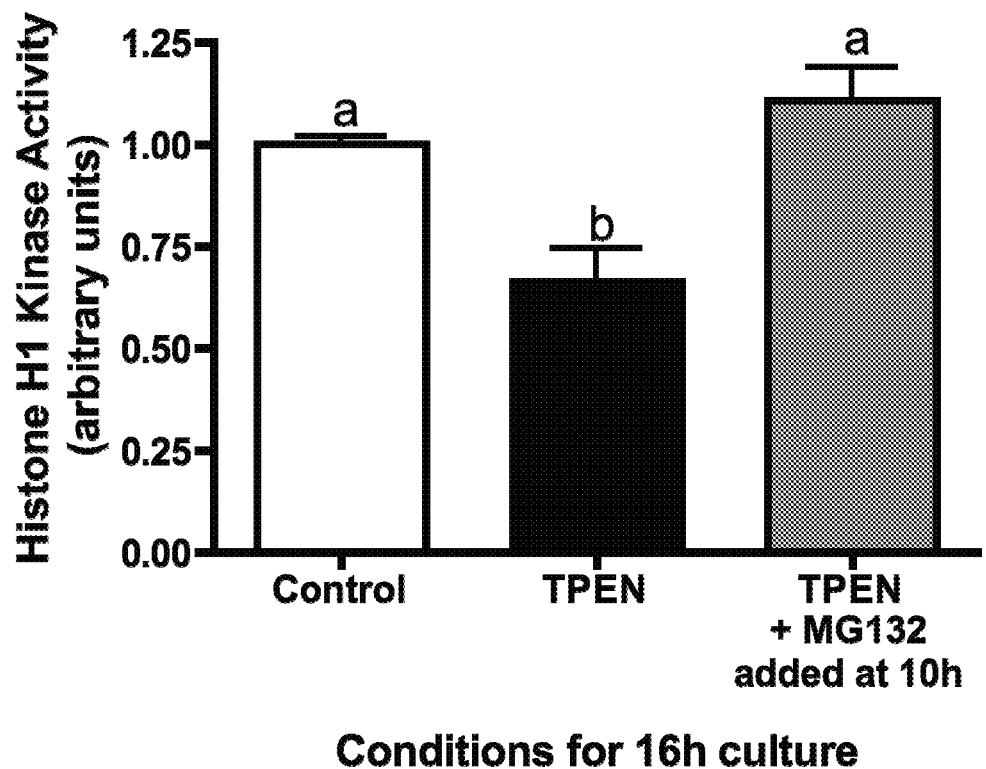
Figure 3:
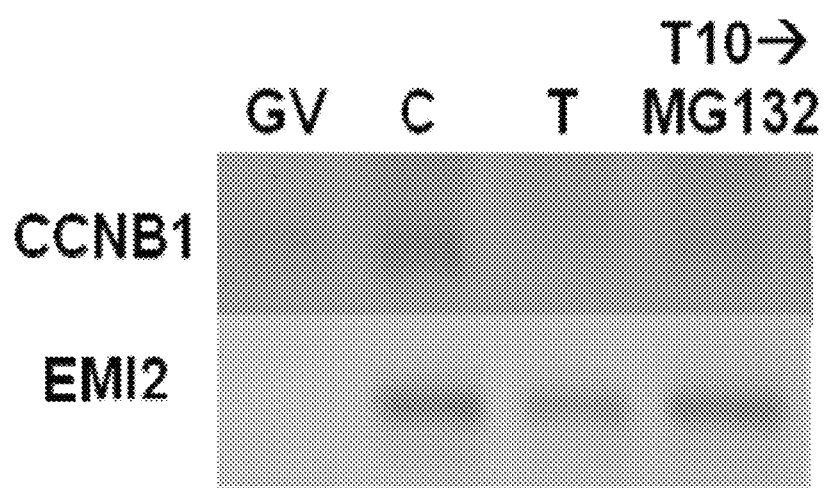
FIG. 3 shows proteasome inhibition only partially restores CCNB1 levels. Western blots for CCNB1 and EMI2 with oocytes cultured in TPEN containing medium for 10 h and transferred to medium containing both TPEN and MG132 for an additional 6 hours.

MII spindles of proteasome treated eggs had varying degrees of organization, with 19% showing aligned metaphase plates (FIG. 2, A.i), while other eggs had slight (31%) to severe (19%) scattering of chromosomes along the length of the spindle (FIG. 2, A.ii, ≤3 misaligned chromosomes, and FIG. 2, A.iii, >3 misaligned chromosomes, respectively). Notably, eggs that had divided symmetrically during the first meiotic division frequently had 2 spindles, one in each cell (FIG. 2, A.i). Histone H1 kinase assays of MG132-treated oocytes show that MPF activity was increased compared to oocytes cultured with TPEN alone (FIG. 2, B). CCNB1 protein levels were only slightly increased in MG132 treated-oocytes (FIG. 3), showing that proteasome inhibition could partially, but not completely restore Cyclin B1, likely contributing to the observed partial rescue.

Figure 4:
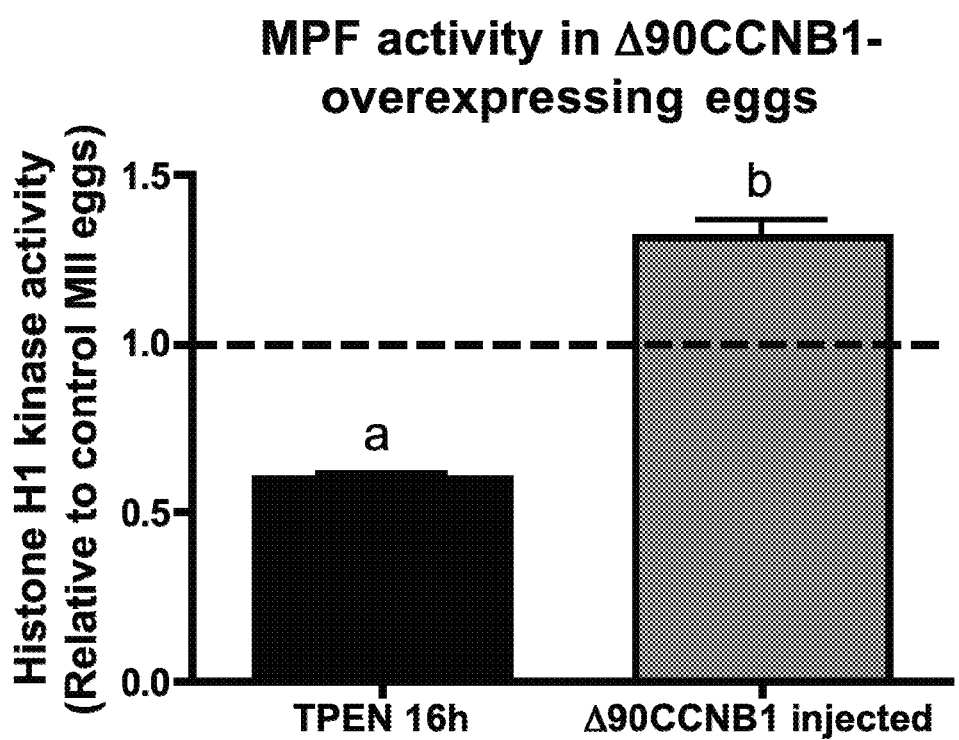
FIG. 4 shows non-degradable CCNB1 increases MPF activity in zinc insufficient oocytes. GV oocytes cultured in TPEN containing medium were injected with CCNB1(Δ90)-EGFP cRNA after 10 to 12.5 hours of a 16 hour IVM culture. Histone H1 kinase activity is shown as densitometric analysis for at least 6 individual oocytes per group. Error bars show SEM and letters indicate significant differences according to ANOVA with Bonferroni post-hoc test (P<0.01).

Expression of Non-Degradable CyclinB1 Increases MPF Activity in Zinc-Insufficient Oocytes Since proteasome inhibition was an indirect and somewhat non-specific way to increase CCNB1, we also decided to test more directly whether increasing CCNB1 could rescue MPF activity by injecting oocytes with cRNA coding for an EGFP-fused non-degradable form of CCNB1, $\Delta 90$, containing an N-terminal truncation that removes APC/C interaction domain, preventing ubiquitinylation upon APC/C activation. Oocytes were cultured in TPEN-containing medium for 10 to 12.5 hours prior to injection to allow meiosis I progression before increasing CCNB1. Oocytes were cultured for 3 to 6 hours more in the presence of TPEN to allow protein expression. It was previously reported that expression of CCNB1 ($\Delta 90$)-EGFP led to a partial rescue of the zinc-insufficient spindle phenotype, with 89% of those oocytes that had completed the first meiotic division by the end of culture displaying some degree of spindle-like structures, although most of these spindles were quite disorganized, with chromosomes spread along the length of the spindle microtubules (Bernhardt et al., 2010). Here, we also show that MPF activity in injected cells is significantly increased compared to uninjected oocytes cultured in the presence of TPEN for the same period of time (FIG. 4). MPF levels in injected eggs were, in fact, slightly higher than in control IVM MII eggs.

The Emi2 Zinc-Binding Region (ZBR) Contributes to Progression Through the MI-MII Transition Emi2 is required for MI-MII transition (Liu et al., 2006; Madgwick et al., 2006; Ohe et al., 2007), it is an important component of cytostatic factor (CSF) activity needed for establishment and maintenance of MII arrest (Masui and Markert, 1971; Schmidt et al., 2005; Shoji et al., 2006; Tung et al., 2005), and it is degraded rapidly upon egg activation (Madgwick et al., 2006; Wu and Kornbluth, 2008). As these are the same events for which zinc seems to be required, it was hypothesized that zinc may be working through regulation of Emi2, so it was important to test whether zinc binding was required for MII arrest in mouse eggs. Work in Xenopus has shown that the N-terminal ZBR is required for XEmi2 APC/C inhibitory function in vitro (Schmidt et al., 2005), and recent work has shown that a functional Emi2 ZBR contributes to the ability of Emi2 to artificially arrest oocytes at MI, when expressed prematurely (Suzuki et al., 2010a). Since the first and second meiotic divisions are regulated differentially (Tsurumi et al., 2004), we chose to examine the importance of the Emi2 ZBR in the more physiological context of MII arrest. GV stage oocytes were injected with Emi2 MO targeted against a sequence specific to the Emi2 5' UTR, as has been previously reported (Madgwick et al., 2006), and were held in IBMX containing medium for 5-6 hours. Oocytes were then cultured in IVM medium until the first polar body was produced (7.5 to 11 hours of IVM). It was noted that oocytes injected with Emi2 MO underwent accelerated first meiotic divisions, with polar bodies present in a higher proportion of MO-injected oocytes than uninjected controls by 7 hours of IVM. This acceleration of meiotic maturation was likely related to the amount of time oocytes were held in IBMX containing medium, as no such acceleration of first polar body formation was reported with oocytes held for only 2 hours in milrinone containing medium after Emi2 MO injection (Madgwick et al., 2006). Oocytes were injected with either wild-type Emi2 or Emi2-0573A cRNA, both lacking the MO-targeted UTR sequence to rescue the Emi2 knockdown, within 2 hours of polar body formation, and cultured for the remainder of a 15 hour total IVM culture. C573 is the first of 8 putative zinc-binding residues in the Emi2 ZBR (Schmidt et al., 2005; Suzuki et al., 2010a).

Figure 5:
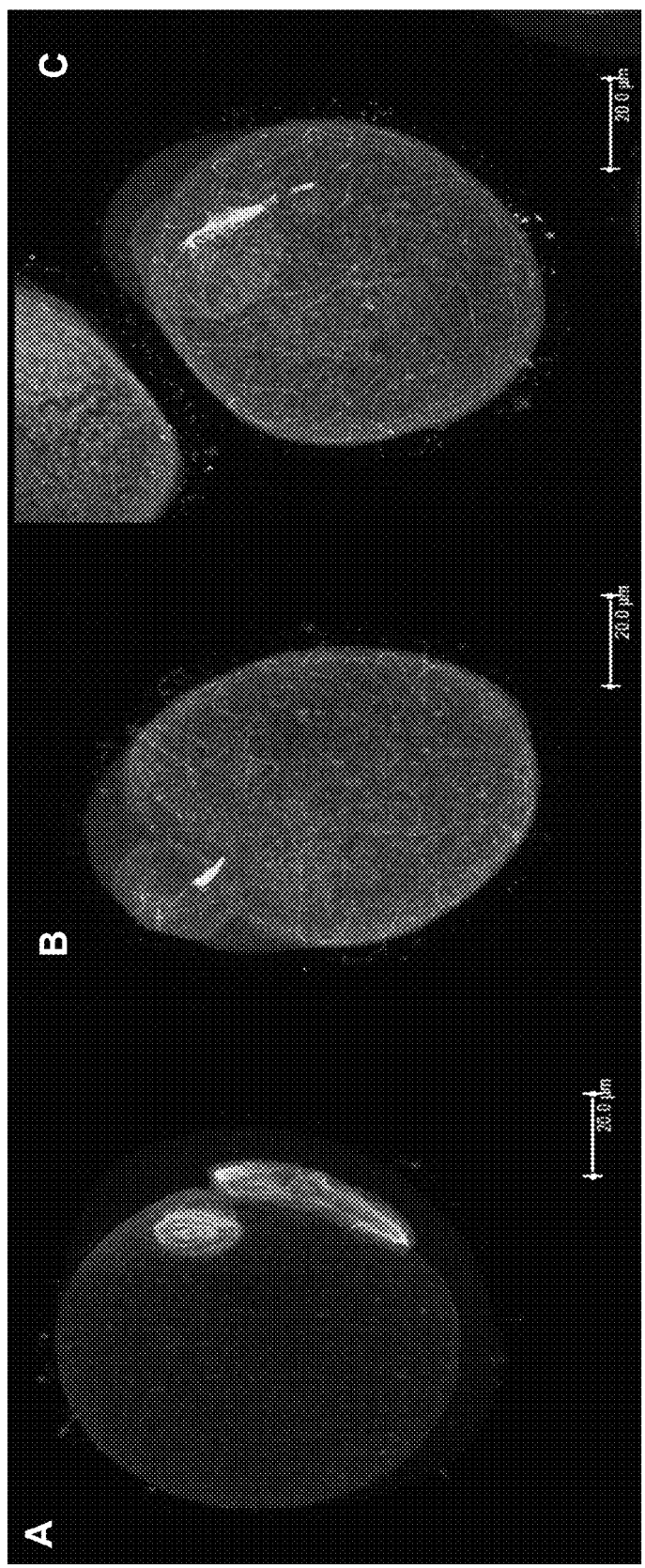
FIGS. 5A-I show Emi2 knockdown phenotype resembles zinc insufficiency. Uninjected in vitro matured eggs have normal MII spindles (A), while the majority of oocytes injected with Emi2 MO (B-F) or Emi2 siRNA (H and I) do not form MII spindles. MO and siRNA injected oocytes show varying degrees of midbody microtubule retention, and frequently have large polar bodies. Occasionally oocytes divide incorrectly to produce two chromatin-containing polar bodies with an empty oocyte (F), or progress through an apparent second meiotic division to produce a second polar body (G). MO injected oocytes were held in IBMX containing medium for 5-6 h prior to a 15 h IVM culture; siRNA injected oocytes were held for 24 h prior to IVM. Projections of confocal Z stacks with actin, tubulin, and DAPI shown in contrast. Bar=20 μm (A-G) or 25 μm (H and I).
Figure 5:
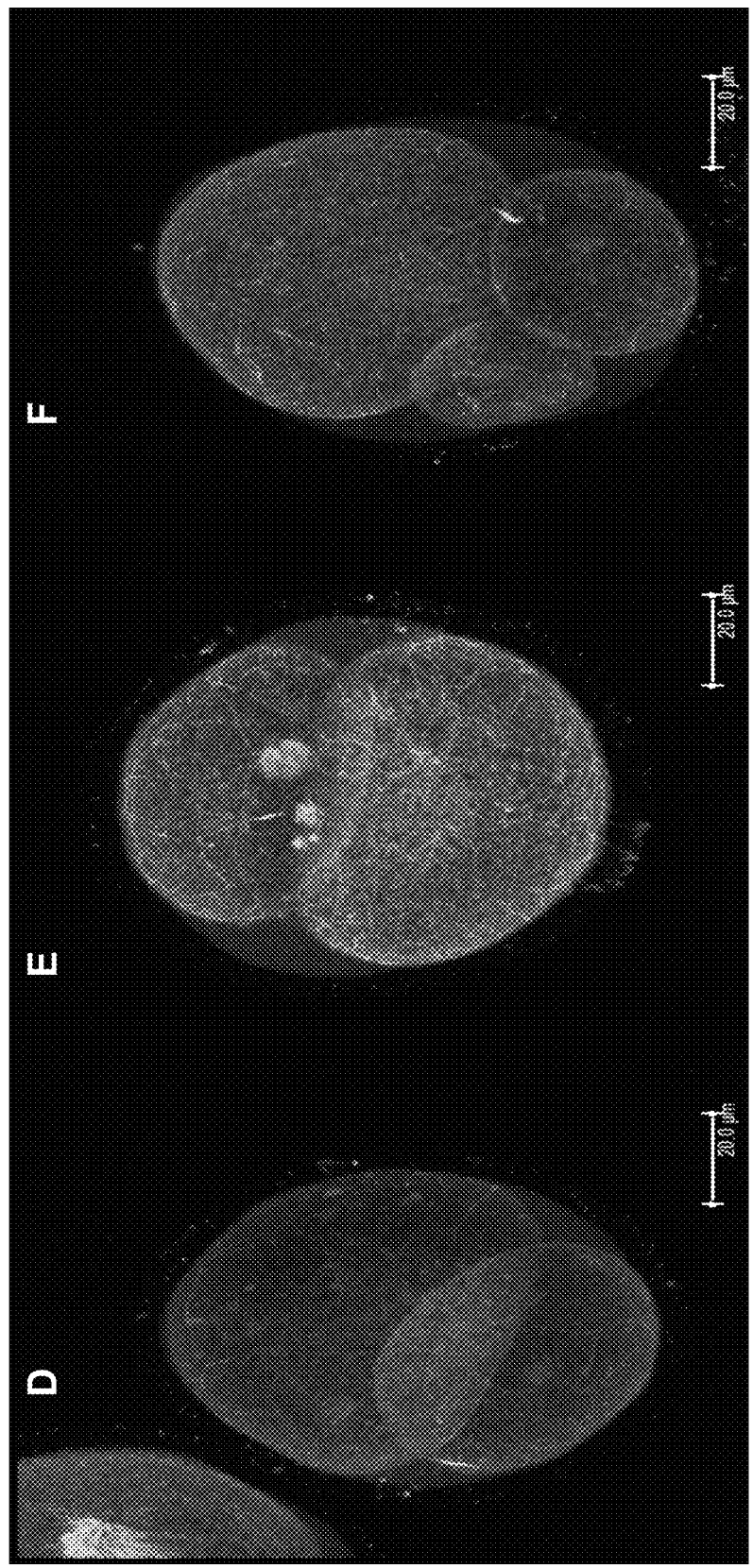
Figure 5:
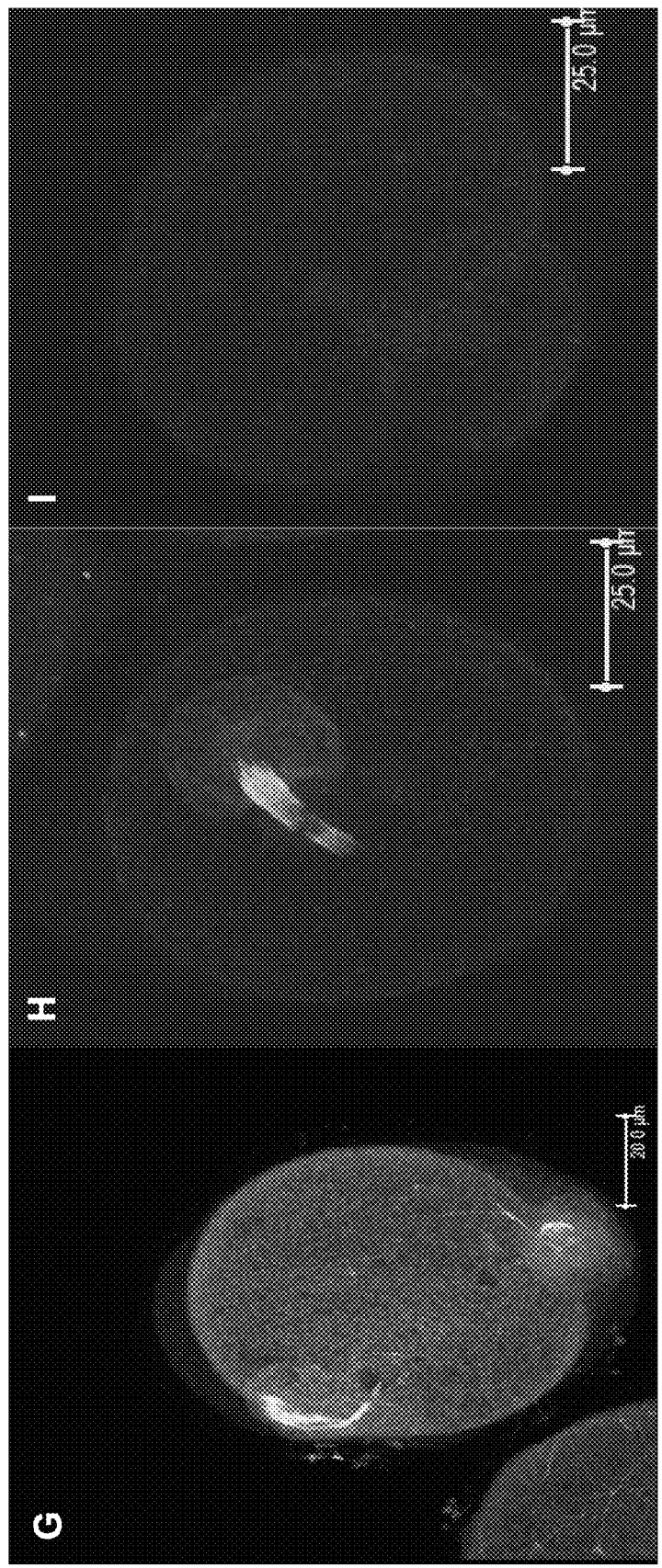

The majority (73%) of oocytes injected with Emi2 MO did not have MII spindles after 15 hours of IVM, and instead had masses of chromatin without discretely visible chromosomes and varying degrees of midbody microtubule retention (FIG. 5). Knockdown of Emi2 during oocyte maturation has previously been described, using both MO (Madgwick et al., 2006) and siRNA (Shoji et al., 2006; Suzuki et al., 2010a) approaches; however, these groups did not report an impact of Emi2 depletion on first polar body size. It was found that MO-injected oocytes frequently divided to produce large first polar bodies, with up to 22% of cells having first polar body diameter>50% that of oocyte diameter, depending on the experiment. In addition to failure of MII spindle formation, disruption of asymmetric division as well as slight acceleration of meiosis I are also characteristics of zinc-insufficient oocytes (Bernhardt et al., 2010; Kim et al., 2010), consistent with the hypothesis that zinc insufficiency interferes with Emi2 function. However, some Emi2 depleted oocytes do go on to produce MII spindles and divide to produce second polar bodies (FIG. 5, (Shoji et al., 2006)). While the present invention is not limited to any particular mechanism and an understanding of the mechanism is not necessary to practice the invention, since MII spindles are never observed in TPEN-treated oocytes, this suggests that either some Emi2 expression may persist in MO-injected oocytes allowing brief MII establishment or that zinc insufficiency could also impact other pathways involved in MII establishment. Similar phenotypes were observed when oocytes were injected with Emi2 siRNA, held in IBMX containing medium for 24 hours, and matured in vitro for 15 hours (FIG. 5).

Figure 6A:
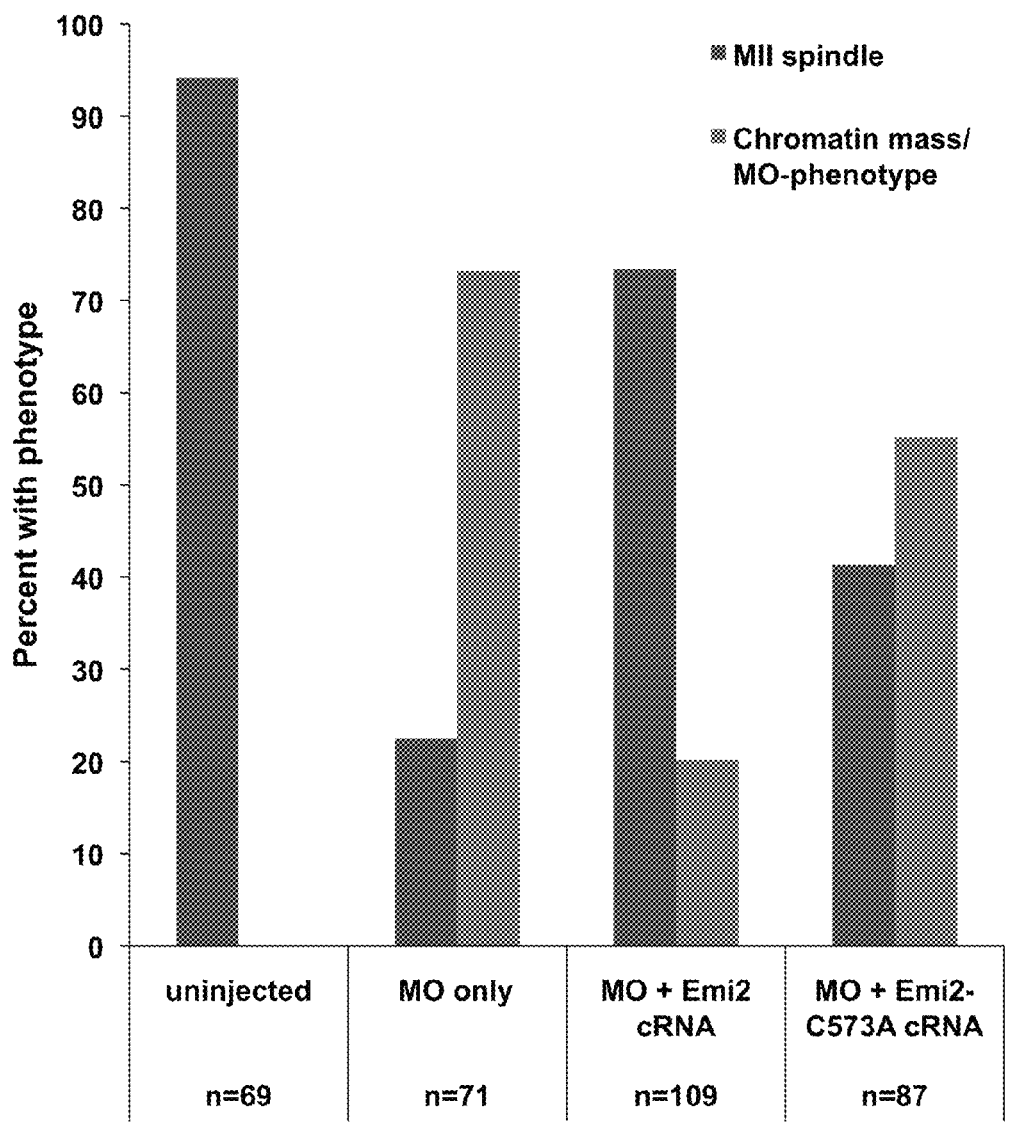
FIGS. 6A-D show intact Emi2 ZBR is required for MI-MII transition. Cumulus-denuded GV oocytes were injected with Emi2 MO, held in IBMX for 5 h, and transferred to IVM medium. Following first polar body extrusion, groups of oocytes were injected with cRNA coding for T7-tagged wild-type Emi2 or for T7-tagged C573A mutated Emi2. Following 15 h total IVM, oocytes were fixed, stained for actin, tubulin, and DNA shown in contrast, imaged by confocal microscopy, and scored for spindle stage (A). 94% of uninjected eggs have normal MII spindles, while 73% of MO-injected oocytes had chromatin masses and partial retention of midbody microtubules. Wild-type Emi2 cRNA rescued MII spindle formation in 73% of oocytes, while ZBR-mutant Emi2 cRNA rescued MII formation in only 41%. Projections of confocal Z stacks are shown for MO injected (B), Emi2 cRNA rescue (C) and Emi2-C573A cRNA rescue.(D). Bar=20 μm.
Figure 6:
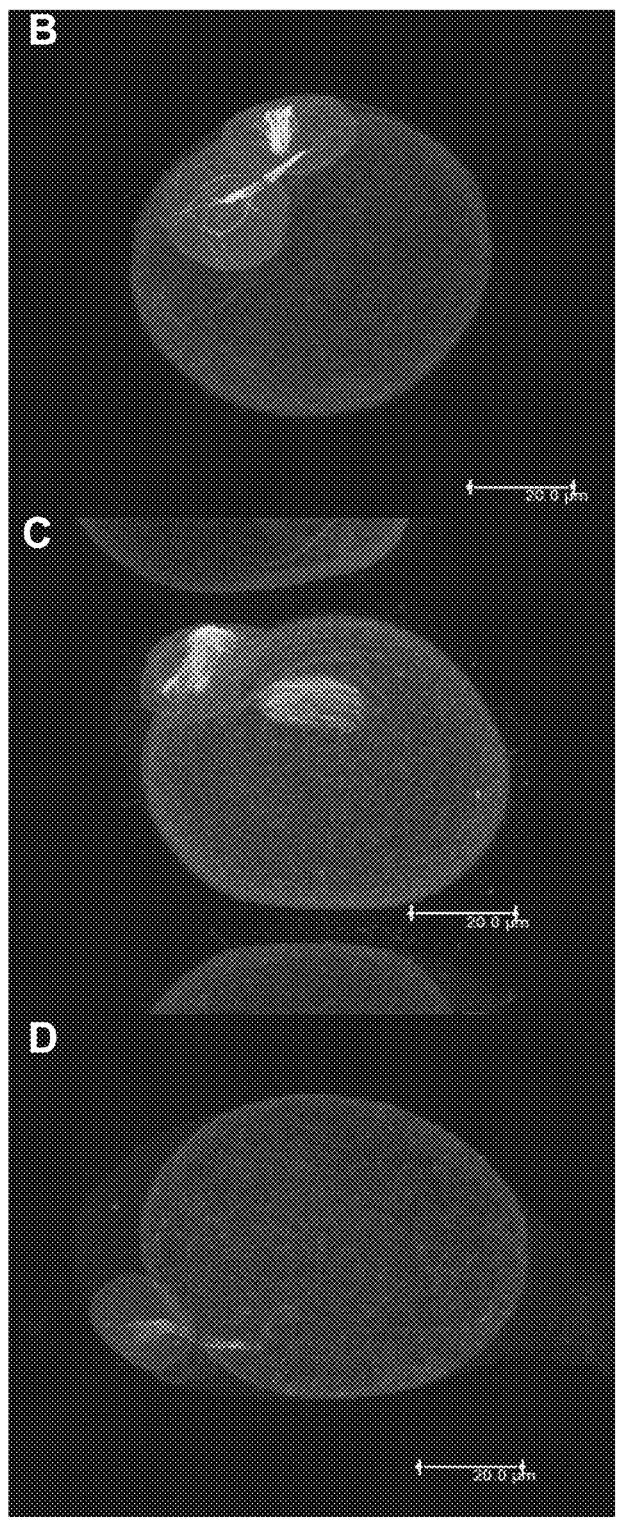

Injection of oocytes with Emi2 cRNA after first polar body extrusion restored MII spindle formation in 73% of cells (FIG. 6). Failure to completely rescue spindle formation may have been due to injection timing, as injection before first polar body extrusion would likely cause MI arrest, as has been reported for injection of Emi2 cRNA into GV oocytes (Madgwick et al., 2006; Suzuki et al., 2010a), while injection too long after the first meiotic division could fail to rescue spindle formation if the reduction in CCNB1 levels can no longer be overcome by restoration of Emi2's APC/C inhibitory activity. Injection of Emi2-C573A cRNA, which contains a mutation in the putative Emi2 ZBR, restored MII spindle formation in only 41% of cells (with a basal level of 23% of oocytes injected with MO only producing MII spindles) (FIG. 6). Therefore, mutation of a single amino acid in the Emi2-ZBR impairs but does not completely abrogate the ability of Emi2 to establish MII arrest. This is consistent with the partially reduced ability of Emi2 ZBR mutants to induce arrest at MI (Suzuki et al., 2010a).

TPEN Interferes with the Ability of Emi2 to Induce Metaphase Arrest

Injection of Emi2 cRNA into GV oocytes prior to IVM results in MI arrest (Madgwick et al., 2006; Suzuki et al., 2010a). While the present invention is not limited to any particular mechanism and an understanding of the mechanism is not necessary to practice the invention, it was hypothesized that zinc insufficiency interferes with the ability of Emi2 to support the MI-MII transition. Therefore, it was sought to be tested whether zinc insufficiency could also impair the ability of Emi2 to induce artificial MI arrest when expressed prematurely. GV oocytes were injected with Emi2 cRNA, held in IBMX containing medium for 2-3 hours to allow overexpression, and transferred to IVM medium with or without 10 µM TPEN for 14 hours. Consistent with previous reports, 100% of Emi2 cRNA-injected oocytes matured in control IVM medium arrested at MI.

Figure 7A:
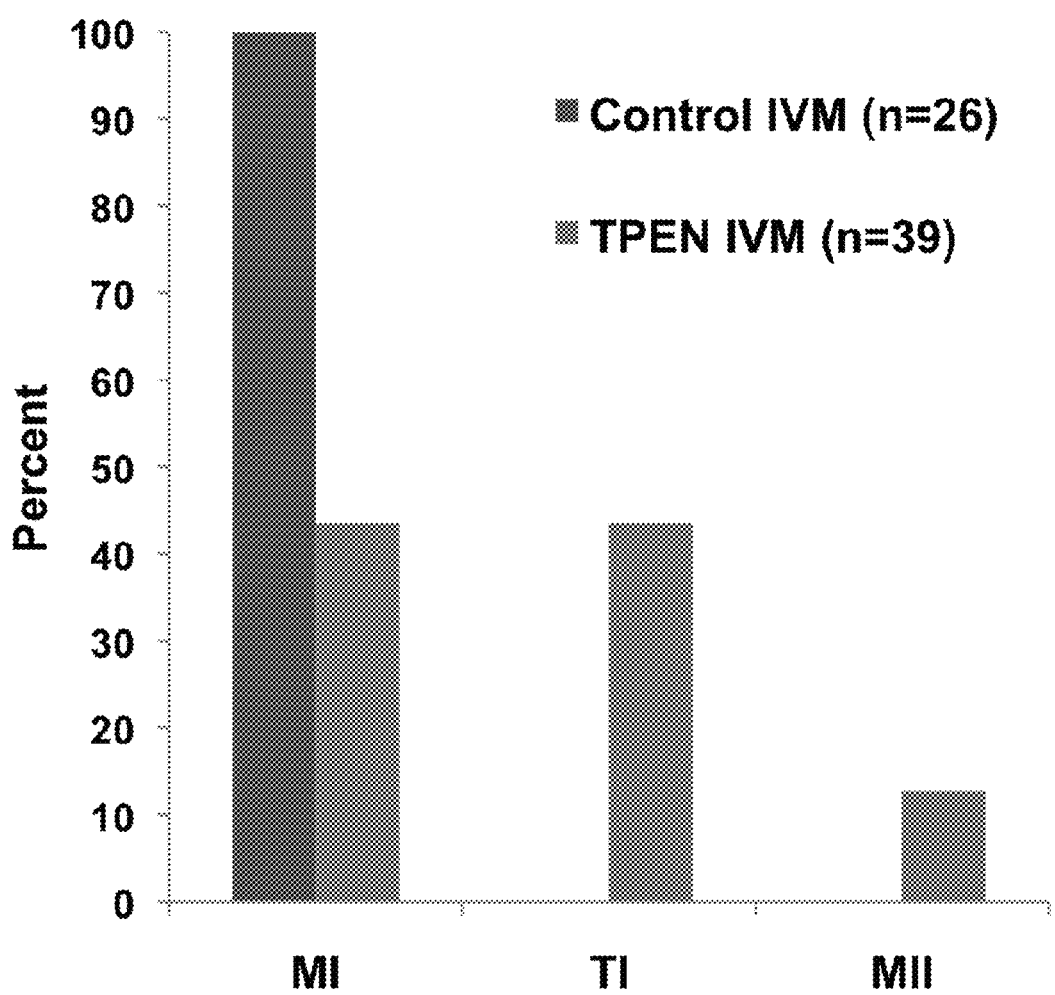
FIGS. 7A-D show TPEN inhibits the ability of Emi2 to maintain metaphase arrest in oocytes. Cumulus-denuded GV oocytes were injected with Emi2 cRNA, held in IBMX for 2-3 h, and transferred to IVM medium for 14 h in control medium or medium containing 10 μM TPEN. Oocytes were fixed, stained for actin, tubulin, and DNA shown in contrast, imaged by confocal microscopy, and scored for spindle stage (A). 100% of Emi2 cRNA-injected oocytes cultured in control medium arrested at MI, while Emi2 expression caused MI arrest in only 44% of oocytes cultured in TPEN containing medium. Projections of confocal Z stacks are shown for Emi2 cRNA-injected oocytes cultured in TPEN containing medium arrested at MI (B), telophase-I (C), and MII (D). Bar=20 μm.
Figure 7:
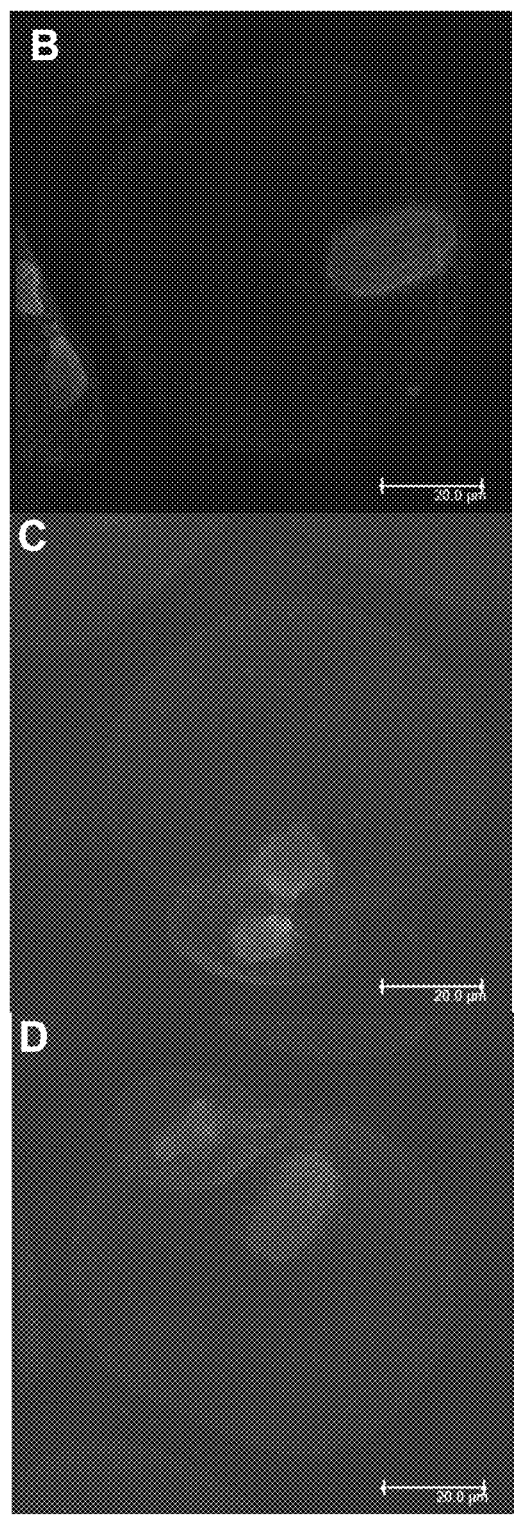

However, only 44% of Emi2 cRNA-injected oocytes arrested at MI when cultured in TPEN containing medium (FIG. 7), showing that TPEN can interfere with the ability of Emi2 to induce metaphase arrest.

MPF Activity Declines After TPEN Treatment of MII Eggs

Figure 8:
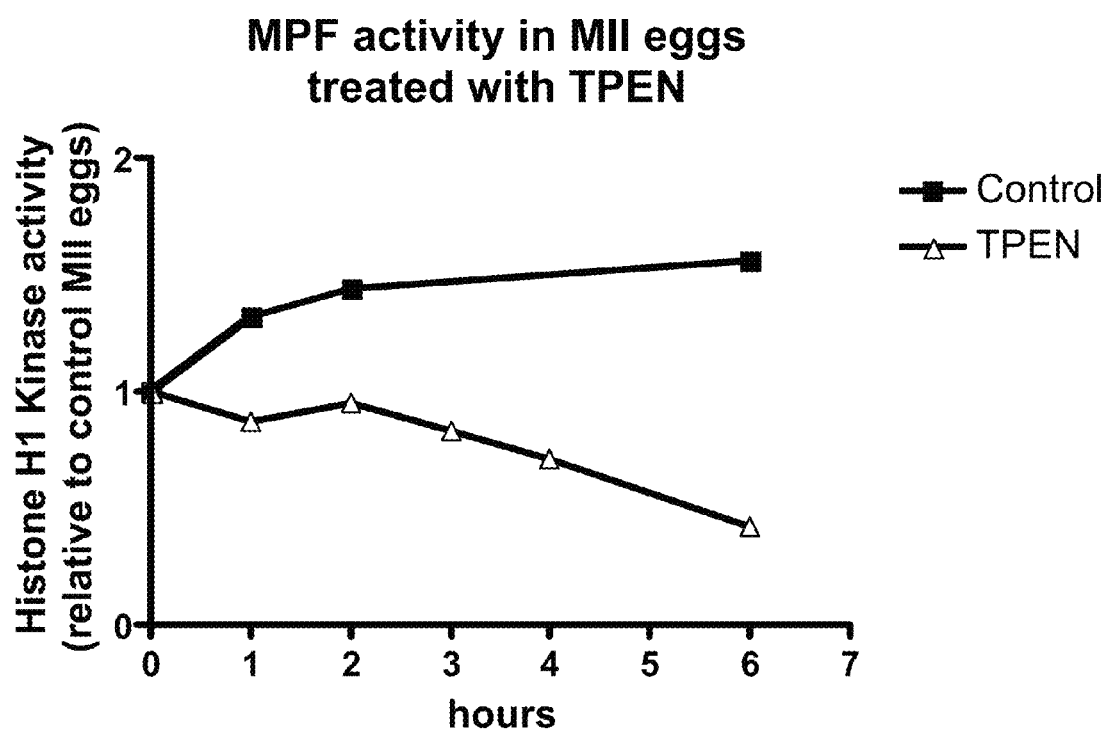
FIG. 8 shows MPF activity declines after TPEN treatment of MII eggs. In vivo ovulated MII eggs were cultured in KSOM medium with or without 10 μM TPEN for 1 to 6 h. Histone H1 and myelin basic protein (MBP) kinase assays were performed on individual eggs; analysis of densitometry after autoradiography is shown with values normalized to that of a control IVM MII egg.

In addition to the involvement of both Emi2 and zinc in establishment and maintenance of MII arrest, recent developments have also drawn attention to the role of zinc at MII exit. Recent reports described a series of zinc exocytosis events (zinc sparks) occurring at fertilization, establishing zinc loss as a hallmark of egg activation (Kim et al., 2011). Additionally, sequestration of zinc using TPEN has been shown to induce egg activation and embryo development (Kim et al., 2011; Suzuki et al., 2010b). Histone H1 and MBP dual kinase assays were performed on individual in vivo ovulated eggs cultured for 1 to 8 hours in KSOM or KSOM containing 10 µM TPEN, to reflect kinase activities of MPF and MAPK, respectively. While MPF activity remained elevated in MII arrested eggs, TPEN treatment caused a decline in MPF activity as soon as 1 hour after treatment was initiated (FIG. 8), consistent with the previously reported decrease in CCNB1 levels in TPEN-treated eggs (Suzuki et al., 2010b). MAPK activity did not change appreciably over the times tested.

Increasing Intracellular Zinc in MII Eggs Prevents Activation

Figure 9A:
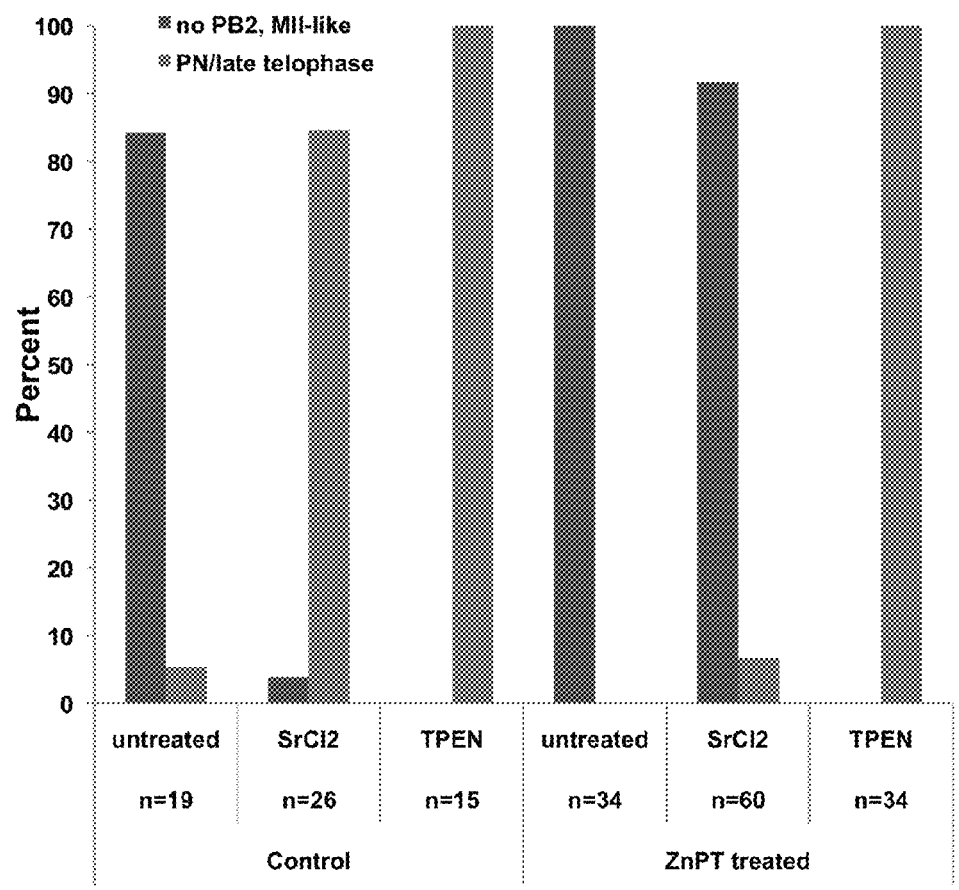
FIGS. 9A and 9B show increasing intracellular zinc in MII eggs prevents activation by SrC12 but not by TPEN. In vivo ovulated MII eggs were treated with 10 μM ZnPT for 5 minutes to increase intracellular zinc, followed by activation with either SrC12 or TPEN. By 6 h post-SrC12 or TPEN treatment, most control oocytes had formed second polar bodies and PN or PN-like structures, while only TPEN caused activation in ZnPT pre-treated eggs (A). Representative bright-field images and three-dimensional projections of confocal Z stacks with actin, tubulin, and DAPI are shown in contrast for each treatment group below the graph. Eggs treated with ZnPT displayed varying degrees of MII-spindle disorganization, ranging from elongated spindles with presence of astral microtubules to scattered chromosomes with sparse tubulin staining Bar =20 μm (B).
Figure 9B:
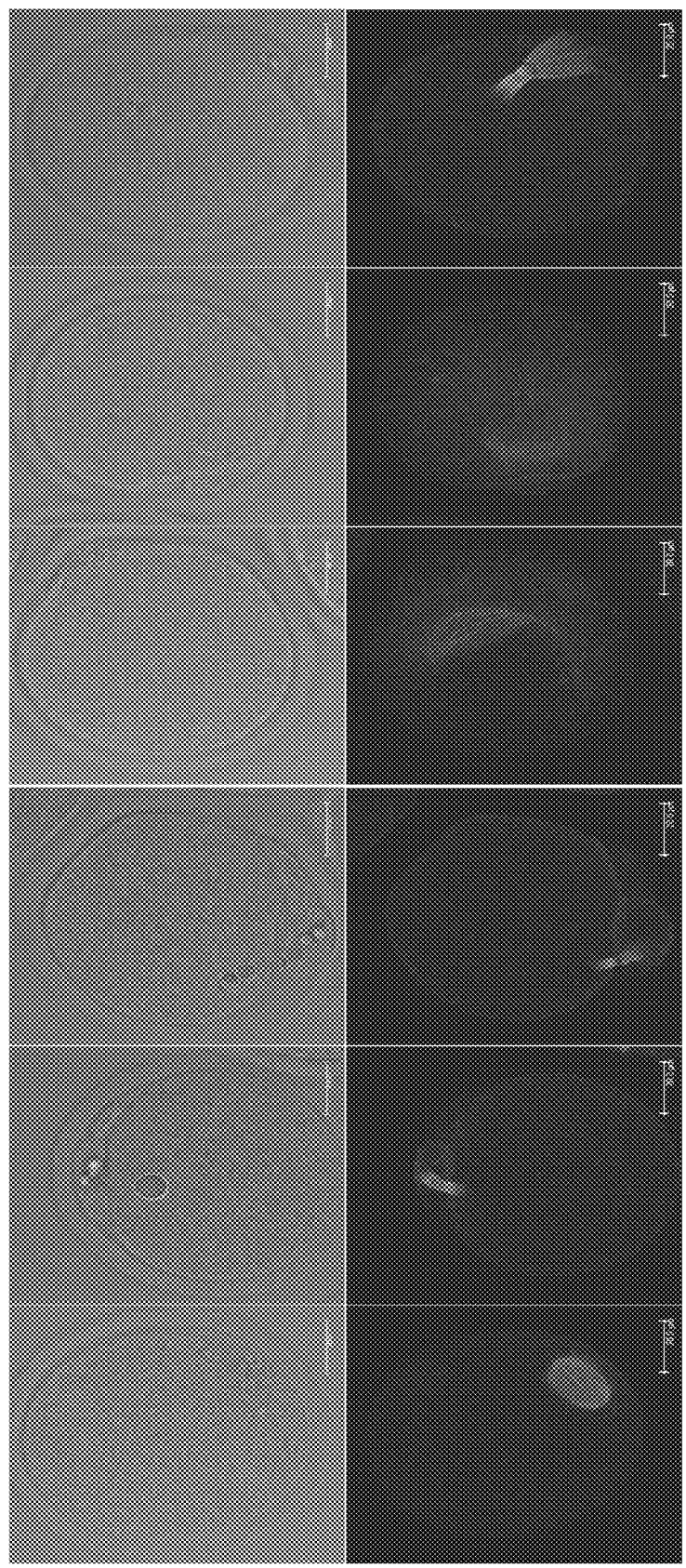

The ability of zinc sequestration to cause egg activation has shown that decreasing availability of intracellular zinc is sufficient to cause meiotic resumption, and the occurrence of zinc sparks demonstrates that this is reduction in zinc is also biologically relevant (Kim et al., 2011; Suzuki et al., 2010b). To further assess the role of zinc in the events of egg activation, it was sought to determine whether this decrease in available zinc is required for egg activation. MII eggs were treated with the ionophore zinc pyrithione (ZnPT) for 5 minutes to increase intracellular zinc. Following a 10-15 minute recovery period, eggs were then treated with activating agents $SrCl_2$ or TPEN. Control MII eggs activated normally, with both $SrCl_2$ and TPEN inducing second polar body formation and formation of pronuclei (PN) or PN-like structures by 6 hours post activation (hpa) (FIG. 9). Eggs pretreated with ZnPT formed second polar bodies and PN-like structures when incubated subsequently with TPEN, but did not show signs of activation after $SrCl_2$ treatment (FIG. 9). ZnPT treatment caused spindle abnormalities in unactivated eggs and eggs treated with $SrCl_2$ following 6 hours of culture, including severely elongated spindle microtubules, presence of astral microtubules, and scattering of chromatin. However, chromosomes remained condensed in these eggs with no indication of cell cycle progression or interphase entry, and this spindle disorganization did not preclude activation by TPEN (which requires an intact spindle (Kubiak et al., 1993; Suzuki et al., 2010b)), indicating that this disorganization likely occurred upon extended culture was not the cause of failed activation by $SrCl_2$. This result also corroborates with our previous results showing that elevation of the zinc quota following egg activation causes reformation of a metaphase-like state (Kim et al., 2011).

Discussion

Zinc is Required for Maintenance of Proper CCNB1 Levels and MPF Activity

During the final stages of oocyte development, intracellular zinc increases by over fifty percent (Kim et al., 2010). Preventing this increase results in meiotic arrest at telophase I and failure to increase CCNB1 levels and establish MII, showing that a tremendous increase in zinc content over a short period of time is required for proper meiotic progression (Bernhardt et al., 2010; Kim et al., 2010). In this Example, it is shown that zinc insufficiency initiated at the end of MI is sufficient to cause meiotic arrest, decreased CCNB1, and reduced MPF activity (FIG. 1 and Table 1). It has been previously shown that oocytes matured in the presence of TPEN for up to 9 hours followed by rescue with endogenous zinc form MII spindles (Kim et al., 2010). This data indicates that the window for zinc action in allowing meiotic progression is at the MI-MII transition. Furthermore, it is shown that increasing CCNB1 activity either via proteasome inhibition to limit degradation or by expression of non-degradable CCNB1 restores MPF activity and partially rescues MII spindle formation in zinc-insufficient oocytes (FIG. 2-4, (Bernhardt et al., 2010)). Restoration of meiotic progression indicates that the major impact of zinc insufficiency on meiotic cell cycle is due to perturbed regulation of CCNB1. Since continued CCNB1 degradation could be an effect of overactive APC/C, and the APC/C inhibitor Emi2 is a zinc-binding protein required for successful MI-MII transition, it was hypothesized that the increase in total cellular zinc acts through modulation of Emi2 activity to initiate MII entry and arrest, and that zinc insufficiency disrupts this effect.

While restoration of CCNB1 dynamics in zinc-insufficient oocytes resulted in MII spindle formation in many cases, these spindles were often disorganized, and failed cytokinesis was frequently observed. These effects are likely due, at least in part, to difficulty in pinpointing rescues to the precise time of the MI-MII transition. In addition, rescue of the zinc-insufficient phenotype by non-degradable CCNB1 was less complete than rescue by proteasome inhibition. This may indicate that other APC/C substrates, such as securin, are being inappropriately targeted for degradation, contributing to the phenotype of zinc insufficiency. Failure of CCNB1 to fully rescue the zinc insufficiency phenotype may indicate other effects of inappropriate APC/C activity, or could reflect additional pathways being impacted by zinc insufficiency.

Murine Emi2 Requires Zinc for Proper Function

Emi2 is a critical component of the cytostatic factor CSF that maintains MII arrest until fertilization (Schmidt et al., 2005; Shoji et al., 2006; Tung et al., 2005). Emi2 is required for MI-MII transition (Liu et al., 2006; Madgwick et al., 2006; Ohe et al., 2007), and Emi2 is degraded rapidly upon fertilization, allowing APC/C activation and MII exit (Hansen et al., 2006; Liu and Maller, 2005; Madgwick et al., 2006; Rauh et al., 2005). Much of the work unraveling pathways regulating Emi2 function has been performed in *Xenopus* oocytes, and while portions of the pathways mediating CSF arrest are conserved in the mouse (Madgwick et al., 2006; Shoji et al., 2006), important differences have also been reported (Perry and Verlhac, 2008; Suzuki et al., 2010a). While Mos/MAPK pathway signaling is known to impact Emi2 stability via p90Rsk in Xenopus (Inoue et al., 2007; Nishiyama et al., 2007), mouse oocytes lacking any p90Rsk isoform are still able to arrest at MII (Dumont et al., 2005), arguing that an alternate pathway may be involved in mammalian oocytes. In addition, xEmi2 exhibits different localization and cannot substitute for murine Emi2 in mouse oocytes (Suzuki et al., 2010a), and the CaMKII and Plx1 mediated pathway that targets Emi2 for degradation upon fertilization in *Xenopus* (Hansen et al., 2006; Liu and Maller, 2005; Rauh et al., 2005) has yet to be clearly demonstrated in a mammalian system. It is proposed that precise modulation of intracellular zinc in mammalian oocytes may represent an additional layer of regulation of MII arrest, acting through the known CSF component, Emi2.

Emi2 contains a zinc-binding region (ZBR) in its C-terminus that is highly conserved among vertebrate species (Schmidt et al., 2005; Suzuki et al., 2010a). A functional ZBR has been shown to be required for APC/C inhibitory activity of *Xenopus* Emi2 in cell extracts and in vitro (Schmidt et al., 2005), and mutation of putative zinc-binding residues in murine Emi2 reduces its ability to induce artificial arrest at MI (Suzuki et al., 2010a) or to support MII entry and arrest (FIG. 6). In addition, the phenotype of Emi2 knockdown closely resembles that of zinc insufficiency during meiotic maturation (FIG. 5). We also show that zinc sequestration inhibits the ability of exogenously expressed Emi2 to cause MI arrest (FIG. 7), and that increasing cellular zinc abundance using ZnPT (A. M. Kim, unpublished) prevents egg activation by SrCl$_2$ (FIG. 9). Together, these data demonstrate that zinc has a critical role in Emi2's ability to support MII and help substantiate a model in which zinc dynamics may act through Emi2 to regulate meiotic progression. Understanding the biochemistry of mammalian Emi2 and the impact of zinc fluxes could also provide insights into differences in Emi2 regulation between mammals and lower vertebrate species.

Model: Zinc Acts as a Switch to Regulate Emi2 During MII Establishment, Maintenance, and Exit Achieving and maintaining robust MII arrest is necessary for successful reproduction; failure to establish MII prevents formation of a fertilizable gamete and can be a cause of infertility, and failure to maintain arrest at MII can lead to infertility as well as teratoma formation due to parthenogenetic activation (Eppig et al., 1996; Hashimoto et al., 1994; Levran et al., 2002). Recent data show that zinc is important in the establishment, maintenance, and exit from MII. Zinc insufficiency during IVM causes failure to establish MII (Bernhardt et al., 2010; Kim et al., 2010). Sequestration of zinc from MII eggs causes activation (Kim et al., 2011) (FIG. 8) (Suzuki et al., 2010a). Increasing intracellular zinc in MII eggs prevents induction of MII exit (FIG. 9), and increasing zinc content just after activation causes return to a metaphase-like state (Kim et al., 2011). These actions of zinc directly parallel the events in which Emi2 also has a critical role. Furthermore, zinc levels increase over the course of oocyte maturation (Kim et al., 2010), and zinc loss via zinc sparks is a hallmark of egg activation (Kim et al., 2011), concomitant with the increase and decrease in Emi2 activity with MII entry and exit, respectively. Combined with the role of zinc in Emi2 function corroborated by the data presented in this Example, while the present invention is not limited to any particular model or mechanism, nor is an understanding of such model or mechanism necessary to practice the present invention, it is believed that Emi2 acts as a zinc-sensor, with dynamic fluxes in cellular zinc driving meiotic transitions. Such a system could help oocytes achieve a robust, yet responsive system for controlling meiotic progression by utilizing multiple, intersecting pathways. This model also serves to explain the potential function of the recently described astonishing phenomenon of the zinc sparks (Kim et al., 2011).

REFERENCES

The following references are each herein specifically incorporated by reference as if fully set forth herein:

Bernhardt, M. L., A. M. Kim, T. V. O'Halloran, and T. K. Woodruff 2010. Zinc Requirement During Meiosis I-Meiosis II Transition in Mouse Oocytes Is Independent of the MOS-MAPK Pathway. Biol. Reprod. 84:526-536.

Ducibella, T., and R. Fissore. 2008. The roles of Ca2+, downstream protein kinases, and oscillatory signaling in regulating fertilization and the activation of development. Dev. Biol. 315:257-279.

Dumont, J., M. Umbhauer, P. Rassinier, A. Hanauer, and M. H. Verlhac. 2005. p90Rsk is not involved in cytostatic factor arrest in mouse oocytes. J. Cell Biol. 169:227-231.

Eppig, J. J., K. Wigglesworth, D. S. Varnum, and J. H. Nadeau. 1996. Genetic regulation of traits essential for spontaneous ovarian teratocarcinogenesis in strain LT/Sv mice: aberrant meiotic cell cycle, oocyte activation, and parthenogenetic development. Cancer Res. 56:5047-5054.

Gautier, J., J. Minshull, M. Lohka, M. Glotzer, T. Hunt, and J. L. Maller. 1990. Cyclin is a component of maturation-promoting factor from *Xenopus*. Cell. 60:487-494.

Hansen, D. V., J. J. Tung, and P. K. Jackson. 2006. CaMKII and polo-like kinase 1 sequentially phosphorylate the cytostatic factor Emi2/XErp1 to trigger its destruction and meiotic exit. Proc. Natl. Acad. Sci. U.S.A. 103:608-613.

Hashimoto, N., N. Watanabe, Y. Furuta, H. Tamemoto, N. Sagata, M. Yokoyama, K. Okazaki, M. Nagayoshi, N. Takeda, Y. Ikawa, and et al. 1994. Parthenogenetic activation of oocytes in c-mos-deficient mice. Nature. 370:68-71.

Holt, J. E., J. Weaver, and K. T. Jones. 2010. Spatial regulation of APCCdh1-induced cyclin B1 degradation maintains G2 arrest in mouse oocytes. Development. 137:1297-1304.

Ibanez, E., A. Sanfins, C. M. Combelles, E. W. Overstrom, and D. F. Albertini. 2005. Genetic strain variations in the metaphase-II phenotype of mouse oocytes matured in vivo or in vitro. Reproduction (Cambridge, England). 130:845-855.

Igarashi, H., J. G. Knott, R. M. Schultz, and C. J. Williams. 2007. Alterations of PLCbeta1 in mouse eggs change calcium oscillatory behavior following fertilization. Dev. Biol. 312: 321-330.

Inoue, D., M. Ohe, Y. Kanemori, T. Nobui, and N. Sagata. 2007. A direct link of the Mos-MAPK pathway to Erp1/Emi2 in meiotic arrest of *Xenopus laevis* eggs. Nature. 446:1100-1104.

Kim, A. M., M. L. Bernhardt, B. Y. Kong, R. W. Ahn, S. Vogt, T. K. Woodruff, and T. V. O'Halloran. 2011. Zinc Sparks Are Triggered by Fertilization and Facilitate Cell Cycle Resumption in Mammalian Eggs. ACS Chem Biol.

Kim, A. M., S. Vogt, T. V. O'Halloran, and T. K. Woodruff. 2010. Zinc availability regulates exit from meiosis in maturing mammalian oocytes. Nat Chem Biol. 6:674-681.

Kubiak, J. Z., M. Weber, H. de Pennart, N. J. Winston, and B. Maro. 1993. The metaphase II arrest in mouse oocytes is controlled through microtubule-dependent destruction of cyclin B in the presence of CSF. EMBO J. 12:3773-3778.

Laemmli, U. K. 1970. Cleavage of structural proteins during the assembly of the head of bacteriophage T4. Nature. 227:680-685.

Levran, D., J. Farhi, H. Nahum, M. Glezerman, and A. Weissman. 2002. Maturation arrest of human oocytes as a cause of infertility: case report. Hum. Reprod. 17:1604-1609.

Liu, J., B. Grimison, A. L. Lewellyn, and J. L. Maller. 2006. The anaphase-promoting complex/cyclosome inhibitor Emi2 is essential for meiotic but not mitotic cell cycles. J. Biol. Chem. 281:34736-34741.

Liu, J., and J. L. Maller. 2005. Calcium elevation at fertilization coordinates phosphorylation of XErp1/Emi2 by Plx1 and CaMK II to release metaphase arrest by cytostatic factor. Curr. Biol. 15:1458-1468.

Lohka, M. J., M. K. Hayes, and J. L. Maller. 1988. Purification of maturation-promoting factor, an intracellular regulator of early mitotic events. Proc. Natl. Acad. Sci. U.S.A. 85:3009-3013.

Madgwick, S., D. V. Hansen, M. Levasseur, P. K. Jackson, and K. T. Jones. 2006. Mouse Emi2 is required to enter meiosis II by reestablishing cyclin B1 during interkinesis. J. Cell Biol. 174:791-801.

Madgwick, S., and K. T. Jones. 2007. How eggs arrest at metaphase II: MPF stabilisation plus APC/C inhibition equals Cytostatic Factor. Cell division. 2:4.

Madgwick, S., V. L. Nixon, H. Y. Chang, M. Herbert, M. Levasseur, and K. T. Jones. 2004. Maintenance of sister chromatid attachment in mouse eggs through maturation-promoting factor activity. Dev. Biol. 275:68-81.

Masui, Y., and C. L. Markert. 1971. Cytoplasmic control of nuclear behavior during meiotic maturation of frog oocytes. J. Exp. Zool. 177:129-145.

Morgan, D. O. 1995. Principles of CDK regulation. Nature. 374:131-134.

Murray, A. W., M. J. Solomon, and M. W. Kirschner. 1989. The role of cyclin synthesis and degradation in the control of maturation promoting factor activity. Nature. 339:280-286.

Nishiyama, T., K. Ohsumi, and T. Kishimoto. 2007. Phosphorylation of Erp1 by p90rsk is required for cytostatic factor arrest in Xenopus laevis eggs. Nature. 446:1096-1099.

Ohe, M., D. Inoue, Y. Kanemori, and N. Sagata. 2007. Erp1/Emi2 is essential for the meiosis I to meiosis II transition in *Xenopus* oocytes. Dev. Biol. 303:157-164.

Perry, A. C., and M. H. Verlhac. 2008. Second meiotic arrest and exit in frogs and mice. EMBO reports. 9:246-251.

Rauh, N. R., A. Schmidt, J. Bormann, E. A. Nigg, and T. U. Mayer. 2005. Calcium triggers exit from meiosis II by targeting the APC/C inhibitor XErp1 for degradation. Nature. 437:1048-1052.

Schindler, K., and R. M. Schultz. 2009. CDC14B acts through FZR1 (CDH1) to prevent meiotic maturation of mouse oocytes. Biol. Reprod. 80:795-803.

Schmidt, A., P. I. Duncan, N. R. Rauh, G. Sauer, A. M. Fry, E. A. Nigg, and T. U. Mayer. 2005. Xenopus polo-like kinase Plx1 regulates XErp1, a novel inhibitor of APC/C activity. Genes Dev. 19:502-513.

Schmidt, A., N. R. Rauh, E. A. Nigg, and T. U. Mayer. 2006. Cytostatic factor: an activity that puts the cell cycle on hold. J. Cell Sci. 119:1213-1218.

Shoji, S., N. Yoshida, M. Amanai, M. Ohgishi, T. Fukui, S. Fujimoto, Y. Nakano, E. Kajikawa, and A. C. Perry. 2006. Mammalian Emi2 mediates cytostatic arrest and transduces the signal for meiotic exit via Cdc20. EMBO J. 25:834-845.

Suzuki, T., E. Suzuki, N. Yoshida, A. Kubo, H. Li, E. Okuda, M. Amanai, and A. C. Perry. 2010a. Mouse Emi2 as a distinctive regulatory hub in second meiotic metaphase. Development. 137:3281-3291.

Suzuki, T., N. Yoshida, E. Suzuki, E. Okuda, and A. C. Perry. 2010b. Full-term mouse development by abolishing $Zn^{2+}$-dependent metaphase II arrest without $Ca^{2+}$ release. Development. 137:2659-2669.

Svoboda, P., P. Stein, H. Hayashi, and R. M. Schultz. 2000. Selective reduction of dormant maternal mRNAs in mouse oocytes by RNA interference. Development. 127:4147-4156.

Tsurumi, C., S. Hoffmann, S. Geley, R. Graeser, and Z. Polanski. 2004. The spindle assembly checkpoint is not essential for CSF arrest of mouse oocytes. J. Cell Biol. 167:1037-1050.

Tung, J. J., D. V. Hansen, K. H. Ban, A. V. Loktev, M. K. Summers, J. R. Adler, 3rd, and P. K. Jackson. 2005. A role for the anaphase-promoting complex inhibitor Emi2/XErp1, a homolog of early mitotic inhibitor 1, in cytostatic factor arrest of *Xenopus* eggs. Proc. Natl. Acad. Sci. U.S.A. 102:4318-4323.

Wu, J. Q., and S. Kornbluth. 2008. Across the meiotic divide-CSF activity in the post-Emi2/XErp1 era. J. Cell Sci. 121:3509-3514.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method comprising: treating a cell in meiotic arrest with a Zn-binding moiety such that meiosis is resumed, and contacting said cell with zinc replete medium such that said cell progresses from metaphase I (MI) to metaphase II (MII).

2. The method of claim 1, wherein said Zn-binding moiety is configured to coordinate one or more Zn ions.

3. A method comprising: treating a fertilized, but un-activated, oocyte with a Zn-binding moiety such that oocyte activation occurs, and contacting said oocyte with zinc replete medium such that said oocyte progresses from metaphase I (MI) to metaphase II (MII).

4. The method of claim 3, wherein said oocyte is un-activated due to lack of sperm PLC activity.

5. The method of claim 3, wherein said oocyte is fertilized by in-vitro fertilization (IVF) methods.

6. The method of claim 3, wherein said oocyte is fertilized by cytoplasmic sperm injection (ICSI).

7. The method of claim 3, wherein said Zn-binding moiety is configured to coordinate one or more Zn ions.

* * * * *